(12) United States Patent
Owens et al.

(10) Patent No.: US 9,023,353 B2
(45) Date of Patent: May 5, 2015

(54) ANTI-(+)—METHAMPHETAMINE MONOCLONAL ANTIBODIES

(71) Applicant: Board of Trustees University of Arkansas, Little Rock, AR (US)

(72) Inventors: Samuel Michael Owens, Little Rock, AR (US); Ralph Henry, Fayetteville, AR (US); Alicia Brown, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 13/802,688

(22) Filed: Mar. 13, 2013

(65) Prior Publication Data

US 2014/0271686 A1       Sep. 18, 2014

(51) Int. Cl.
*A61K 39/395*       (2006.01)
*C07K 16/44*        (2006.01)

(52) U.S. Cl.
CPC ...................... *C07K 16/44* (2013.01)

(58) Field of Classification Search
None
See application file for complete search history.

(56) References Cited

U.S. PATENT DOCUMENTS

| | | | |
|---|---|---|---|
| 4,041,076 | A | 8/1977 | Avenia et al. |
| 4,329,281 | A | 5/1982 | Christenson et al. |
| 4,341,758 | A | 7/1982 | Sakakibara et al. |
| 4,517,290 | A | 5/1985 | Iwasa et al. |
| 4,816,567 | A | 3/1989 | Cabilly et al. |
| 5,041,076 | A | 8/1991 | Kantor |
| 5,135,863 | A | 8/1992 | Hu et al. |
| 5,141,850 | A | 8/1992 | Cole et al. |
| 5,160,701 | A | 11/1992 | Brown, III et al. |
| 5,238,652 | A | 8/1993 | Sun et al. |
| 5,328,828 | A | 7/1994 | Hu et al. |
| 5,415,994 | A | 5/1995 | Imrich et al. |
| 5,451,504 | A | 9/1995 | Fitzpatrick et al. |
| 5,492,841 | A | 2/1996 | Craig |
| 5,501,987 | A | 3/1996 | Ordonez et al. |
| 5,545,806 | A | 8/1996 | Lonberg et al. |
| 5,545,807 | A | 8/1996 | Surani et al. |
| 5,559,041 | A | 9/1996 | Kang et al. |
| 5,569,825 | A | 10/1996 | Lonberg et al. |
| 5,620,890 | A | 4/1997 | Kamps-Holtzapple et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,690,942 | A | 11/1997 | Hjorth |
| 5,976,812 | A | 11/1999 | Huber et al. |
| 6,054,561 | A * | 4/2000 | Ring .................. 530/388.1 |
| 6,087,184 | A | 7/2000 | Magginetti et al. |
| 6,306,616 | B1 | 10/2001 | Shindelman |
| 6,358,710 | B1 | 3/2002 | Graves et al. |
| 6,669,937 | B2 * | 12/2003 | Owens et al. .......... 424/142.1 |
| 7,037,669 | B2 | 5/2006 | Zheng et al. |
| 7,202,348 | B2 * | 4/2007 | Owens et al. .......... 530/388.9 |
| 7,294,649 | B2 | 11/2007 | Hui et al. |
| 7,371,829 | B2 | 5/2008 | McConnell et al. |
| 7,674,884 | B2 * | 3/2010 | Elson et al. .......... 530/388.22 |
| 7,858,756 | B2 * | 12/2010 | Owens et al. .......... 530/388.1 |
| 2001/0051158 | A1 | 12/2001 | Owens et al. |
| 2003/0119083 | A1 | 6/2003 | Owens et al. |
| 2003/0171435 | A1 | 9/2003 | Pouletty et al. |
| 2004/0242848 | A1 | 12/2004 | Owens et al. |
| 2007/0207145 | A1 | 9/2007 | Owens et al. |
| 2010/0055126 | A1 | 3/2010 | Owens et al. |
| 2013/0296537 | A1 | 11/2013 | Owens et al. |

FOREIGN PATENT DOCUMENTS

| | | |
|---|---|---|
| EP | 0239400 A2 | 9/1987 |
| EP | 0343346 A1 | 11/1989 |
| EP | 0375422 A2 | 6/1990 |
| EP | 0574782 A2 | 12/1993 |
| EP | 1331219 A1 | 7/2003 |
| WO | 86/01533 A1 | 3/1986 |
| WO | 92/03163 A1 | 3/1992 |
| WO | 97/49732 A1 | 12/1997 |
| WO | 01/57182 A2 | 8/2001 |
| WO | 01/81424 A1 | 11/2001 |
| WO | 2004/050032 A2 | 6/2004 |
| WO | 2005/093417 A1 | 10/2005 |
| WO | 2007/147122 A2 | 12/2007 |
| WO | WO2007147122 * | 12/2007 |
| WO | WO2008131216 * | 10/2008 |
| WO | 2010/033913 A1 | 3/2010 |
| WO | 2011/131407 A1 | 10/2011 |

OTHER PUBLICATIONS

Rudikoff et al., Proc. Natl. Acad. Sci. USA, 79(6): 1979-1983, Mar. 1982.*
Colman P. M., Research in Immunology, 145:33-36, 1994.*
Bendig M. M., Methods: A Companion to Methods in Enzymology, 8:83-93, 1995.*
MacCallum et al., J. Mol. Biol., 262, 732-745, 1996.*
Wu et al., J. Mol. Biol. 294: 151-162, 1999.*
Paul, William E., Fundamental Immunology, 3rd Edition, Raven Press, New York, Chapt. 8, pp. 292-295, 1993.*
McMillan et al., "Schedule control of quantal and graded dose-effect curves in a drug-drug-saline discrimination", Pharmacology, Biochemistry and Behavior, 2001, pp. 395-402, vol. 68.
McMillan et al., "Discrimination of pentobarbital doses and drug mixtures under fixed-ratio and fixed-interval reinforcement schedules", Behavioral Pharmacology, 2001, pp. 195-208, vol. 12, No. 3.
McMillan et al., "Pharmacokinetic antagonism of (+)-methamphetamine discrimination by a low-affinity monoclonal anti-methamphetamine antibody", Behavioural Pharmacology, 2002, pp. 465-473, vol. 13, Nos. 5 & 6.

(Continued)

*Primary Examiner* — Phuong Huynh
(74) *Attorney, Agent, or Firm* — Polsinelli PC

(57) ABSTRACT

The present invention encompasses compositions and methods for effectively treating at least one symptom or sign of methamphetamine use, or for slowing the rate of (+) methamphetamine entry into the brain of a subject. The method comprises administering an effective amount of an anti-(+) methamphetamine antibody to a subject.

11 Claims, 7 Drawing Sheets
(3 of 7 Drawing Sheet(s) Filed in Color)

(56) References Cited

OTHER PUBLICATIONS

McMillan et al., "Effects of Murine-Derived Anti-Methamphetamine Monoclonal Antibodies on (+)-Methamphetamine Self-Administration in the Rat", J. Pharmacol. Exp. Therapeutics, 2004, pp. 1248-1255, vol. 309, No. 3.
Nam et al., "Production and Characterization of Monoclonal Antibody That Simultaneously Recognizes Methamphetamine and Its Major Metabolite", Biol. Pharm. Bull., 1993, pp. 490-492, vol. 16, No. 5.
Niwaguchi et al., "Determination of d-Methamphetamine in Urine After Administration of d- or dl-Methamphetamine to Rats by Radioimmunoassay Using Optically Sensitive Antiserum", Journal of Forensic Sciences, 1982, pp. 592-597, vol. 27, No. 3.
Notice of Allowance from related U.S. Appl. No. 11/763,948, dated Aug. 19, 2010, 7 pgs.
Notice of Allowance from related U.S. Appl. No. 09/839,549, dated Jul. 11, 2003, 6 pgs.
Notice of Allowance from related U.S. Appl. No. 10/255,462, dated Nov. 24, 2006, 5 pgs.
Office Action from related U.S. Appl. No. 09/839,549, dated Nov. 26, 2001, 12 pgs.
Office Action from related U.S. Appl. No. 10/255,462, dated Jun. 14, 2005, 9 pgs.
Office Action from related U.S. Appl. No. 10/255,462, dated Nov. 16, 2005, 8 pgs.
Office Action from related U.S. Appl. No. 10/255,462, dated Jul. 31, 2006, 4 pgs.
Office Action from related U.S. Appl. No. 11/763,948, dated Sep. 25, 2009, 11 pgs.
Office Action from related U.S. Appl. No. 11/763,948, dated Mar. 24, 2010, 10 pgs.
Office Action from related European Patent Application No. 07798645.3, dated Oct. 26, 2011, 4 pgs.
Owens et al., "Anti-Phencyclidine Fab as a Tool for Studying the Toxic Effects of Phencyclidine", NIH Immuno-toxicology Workshop, Oct. 17 and 18, 1983, Session B—Poster #27, 3 pgs.
Owens et al., "Phencyclidine-Specific Fab Fragments Alter Phencyclidine Disposition in Dogs", Drug Metabolism and Disposition, 1986, pp. 52-58, vol. 14, No. 1.
Owens et al., "Antibodies Against Arylcyclohexylamines and Their Similarities in Binding Specificity with the Phencyclidine Receptor", J. Pharmacol. Exp. Therapeutics, 1988, pp. 472-478, vol. 246, No. 2.
Owens et al., "New Generation of Medications for Drug Abuse", Pharmaceutical News, 1998, p. 44, vol. 5, No. 6.
Owens et al., "Monoclonal anitbodies as pharmacokinetic antagonists for the treatment of (+)-methamphetamine addiction", CNS Neurol Disord Drug Targets, 2011, pp. 892-898, vol. 10, No. 8.
Peakman et al., "Comparison of expression of a humanized monoclonal antibody in mouse NSO myeloma cells and Chinese Hamster Ovary cells", Hum. Antibod. Hybridomas, 1994, pp. 65-74, vol. 5, Nos. 1 and 2.
Peterson et al., "Monoclonal Antibody Form and Function: Manufacturing the Right Antibodies for Treating Drug Abuse", The AAPS Journal, 2006, pp. E383-E390, vol. 8, No. 2, Article 43.
Peterson et al., "Using Hapten Design to Discover Therapeutic Monoclonal Antibodies for Treating Methamphetamine Abuse", J. Pharmacol. Exp. Therapeutics, 2007, pp. 30-39, vol. 322, No. 1.
Peterson et al., "Development and Preclinical Testing of a High-Affinity Single-Chain Antibody against (+)-Methamphetamine", J. Pharmacol. Exp. Therapeutics, 2008, pp. 124-133, vol. 325, No. 1.
Pitas et al., "Anti-Phencyclidine Monoclonal Antibody Binding Capacity Is Not The Only Determinant of Effectiveness, Disproving The Concept That Antibody Capacity Is Easily Surmounted", American Society for Pharmacology and Experimental Therapeutics, 2006, pp. 906-912, vol. 34, No. 6.
Proksch et al., "Pharmacokinetic Mechanisms for Obtaining High Renal Coelimination of Phencyclidine and a Monoclonal Antiphencyclidine Antigen-Binding Fragment of Immunoglobulin G in the Rat", J. Pharmacol. Exp. Therapeutics, 1998, pp. 616-624, vol. 287, No. 2.
Proksch et al., "The Effect of Rate of Drug Administration on the Extend and Time Course of Phencyclidine Distribution in Rat Brain, Testis, and Serum," Drug Metabolism and Disposition, 2000, pp. 742-747, vol. 28, No. 7.
Proksch et al., "Anti-Phencyclidine Monoclonal Antibodies Provide Long-Term Reductions in Brain Phencyclidine Concentrations during Chronic Phencyclidine Administration in Rats", J. Pharmacol. Exp. Therapeutics, 2000, pp. 831-837, vol. 292, No. 3.
Reichert, "Monoclonal antibodies in the clinic", Nature Biotechnology, 2001, pp. 819-822, vol. 19.
Richards et al., "Methamphetamine Abuse and Emergency Department Utilization", West J. Med., 1999, pp. 198-202, vol. 170, No. 4.
Riviere et al., "Spontaneous Locomotor Activity and Pharmacokinetics of Intravenous Methamphetamine and Its Metabolite Amphetamine in the Rat", J. Pharmacol. Exp. Therapeutics, 1999, pp. 1220-1226, vol. 291, No. 3.
Riviere et al., "Disposition of Methamphetamine and Its Metabolite Amphetamine in Brain and Other Tissues in Rats after Intravenous Administration", J. Pharmacol. Exp. Therapeutics, 2000, pp. 1042-1047, vol. 292, No. 3.
Sato et al., "Relapse of Paranoid Psychotic State in Methamphetamine Model of Schizophrenia", Schizophrenia Bulletin, 1992, pp. 115-122, vol. 18, No. 1.
Simmons et al., "Expression of full-length immunoglobulins in *Escherichia coli*: rapid and efficient production of aglycosylated antibodies", J. Immunol. Methods, 2002, pp. 133-147, vol. 263.
Sinacore et al., "Adaptation of Mammalian Cells to Growth in Serum-Free Media", Molecular Biotechnology, 2000, pp. 249-257, vol. 15.
Smith et al., "Immunogenicity and kinetics of distribution and elimination of sheep digoxin-specific IgG and Fab fragments in the rabbit and baboon", Clin. Exp. Immunol., 1979, pp. 384-396, vol. 36.
Smith et al., "Treatment of Life-Threatening Digitalis Intoxication With Digoxin-Specific Fab Antibody Fragments", The New England Journal of Medicine, 1982, pp. 1357-1362, vol. 307, No. 22.
Spector, "Antibodies As Pharmacological Agents", Biochemical Pharmacology, 1976, pp. 2427-2428, vol. 25.
Suttijitpaisal et al., "Immunoassays of Amphetamines: Immunogen Structure vs Antibody Specificity", Asian Pacific Journal of Allergy and Immunology, 1992, pp. 159-164, vol. 10.
Tempest et al. "Reshaping a Human Monoclonal Antibody to Inhibit Human Respiratory Syncytial Virus Infection in Vivo", Biotechnology, 1991, pp. 266-271, vol. 9.
Terazawa et al., "Development of Monoclonal Antibodies Reactive With Methamphetamine Raised Against a New Antigen", Journal of Immunoassay, 1991, pp. 277-291, vol. 12, No. 2.
Tokura et al., "Induction of Methamphetamine-Specific Antibody Using Biodegradable Carboxymethyl-chitin", Analytical Biochemistry, 1987, pp. 117-122, vol. 161.
Usagawa et al., "Preparation of monoclonal antibodies against methamphetamine", J. Immunology Methods, 1989, pp. 111-115, vol. 119.
Valentine et al., "Anti-phencyclidine Monoclonal Fab Fragments Markedly Alter Phencyclidine Pharmacokinetics in Rats", J. Pharmacol. Exp. Therapeutics, 1994, pp. 1079-1085, vol. 269, No. 3.
Valentine et al., "Antiphencyclidine Monoclonal Fab Fragments Reverse Phencyclidine-Induced Behavioral Effects and Ataxia in Rats", J. Pharmacol. Exp. Therapeutics, 1996, pp. 709-716, vol. 278, No. 2.
Valentine et al., "Antiphencyclidine Monoclonal Antibody Therapy Significantly Changes Phencyclidine Concentrations in Brain and Other Tissues in Rats", J. Pharmacol. Exp. Therapeutics, 1996, pp. 717-724, vol. 278, No. 2.
Ward et al., "Radioimmunoassay for the Dual Detection of Amphetamine and Methamphetamine", Journal of Forensic Sciences, 1994, pp. 1486-1496, vol. 39, No. 6.
Whitelegg et al., "WAM: an improved algorithm for modelling antibodies on the WEB", Protein Engineering, 2000, pp. 819-824, vol. 13, No. 12.

(56) References Cited

OTHER PUBLICATIONS

Albertson et al., "Methamphetamine and the Expanding Complications of Amphetamines", West J. Med., 1999, pp. 214-219, vol. 170, No. 4.
Alt et al., "Selective Multiplication of Dihydrofolate Reductase Genes in Methotrexate-resistant Variants of Cultured Murine Cells", J. Biological Chemistry, 1978, pp. 1357-1370, vol. 253, No. 5.
Aoki et al., "Immunoassay for Methamphetamine With a New Antibody", Forensic Science International, 1990, pp. 245-255, vol. 44.
Byrnes-Blake et al., "Generation of anti-(+) methamphetamine antibodies is not impeded by (+) methamphetamine administration during active immunization of rats", International Immunopharmacology, 2001, pp. 329-338, vol. 1.
Byrnes-Blake et al., "Pharmacodynamic mechanisms of monoclonal antibody-based antagonism of (+)-methamphetamine in rats", European J. Pharmacol., 2003, pp. 119-128, vol. 461.
Byrnes-Blake et al., "Monoclonal IgG affinity and treatment time alters antagonism of (+)-methamphetamine effects in rats", European J. Pharmacol., 2005, pp. 86-94, vol. 521.
Carroll et al., "The Synthesis of Haptens and Their Use for the Development of Monoclonal Antibodies for Treating Methamphetamine Abuse", J. Med. Chem., 2009, pp. 7301-7309, vol. 52, No. 22.
Cho et al., "Relevance of Pharmacokinetic Parameters in Animal Models of Methamphetamine Abuse", Synapse, 2001, pp. 161-166, vol. 39.
Choi et al., "Localization of the Epitope in Methamphetamine and Its Antibody Use for the Detection of Methamphetamine and Benzphetamine by Polarization Fluoroimmunoassay", J. Immunoassay, 1995, pp. 263-278, vol. 16, No. 3.
Chothia et al., "Canonical Structures for the Hypervariable Regions of Immunoglobulins", J. Mol. Biol., 1987, pp. 901-917, vol. 196.
Chothia et al., "Conformations of immunoglobulin hypervariable regions", Nature, 1989, pp. 877-883, vol. 342.
Clark, "Antibody humanization: a case of the 'Emperor's new clothes'?", Rev. Immunology Today, 2000, pp. 397-402, vol. 21, No. 8.
Co et al., "Humanized antibodies for antiviral therapy", Proc. Natl. Acad. Sci., 1991, pp. 2869-2873, vol. 88.
Cody, "Detection of D,L-Amphetamine, D,L-Methamphetamine, and Illicit Amphetamine Analogs Using Diagnostic Products Corporation's Amphetamine and Methamphetamine Radioimmunoassay", Journal of Analytical Toxicology, Sep./Oct. 1990, pp. 321-324, vol. 14.
Colbert et al., "Single-Reagent Polarization Fluoroimmunoassay for Amphetamine in Urine", Clin. Chem., 1985, pp. 1193-1195, vol. 31, No. 7.
Colburn, "Specific Antibodies and Fab Fragments to Alter the Pharmacokinetics and Reverse the Pharmacologic/Toxicologic Effects of Drugs", Drug Metab. Rev., 1980, pp. 223-262, vol. 11, No. 2.
Coloma et al., "Novel vectors for the expression of antibody molecules using variable regions generated by polymerase chain reaction", J. Immunological Methods, 1992, pp. 89-104, vol. 152.
Cook et al., "Pharmacokinetics of Methamphetamine Self-Administered to Human Subjects by Smoking S-(+)-Methamphetamine Hydrochloride", Drug Metabolism and Disposition, 1993, pp. 717-723, vol. 21, No. 4.
Danger et al., "Development of murine monoclonal antibodies to methamphetamine and methamphetamine analogues", J. Immunological Methods, 2006, pp. 1-10, vol. 309.
Daniels et al., "Effects of anti-phencyclidine and anti-(+)-methamphetamine monoclonal antibodies alone and in combination on the discrimination of phencyclidine and (+)-methamphetamine by pigeons," Psychopharmacology, 2006, pp. 36-44, vol. 185.
Davis et al., "A Simple Modified Carbodiimide Method for Conjugation of Small-Molecular-Weight Compounds to Immunoglobulin G with Minimal Protein Crosslinking", Analytical Biochemistry, 1981, pp. 402-407, vol. 116.
Extended European Search Report from related European Patent Application No. 07798645.3, mailed Jun. 14, 2010, 7 pgs.

Faraj et al., "Specificity of an Antibody Directed against d-Methamphetamine. Studies with Rigid and Nonrigid Analogs", J. Medicinal Chemistry, 1976, pp. 20-25, vol. 19, No. 1.
Farre et al., "Repeated doses administration of MDMA in humans: pharmacological effects and pharmacokinetics", Psychopharmacology, 2004, pp. 364-375, vol. 173.
Geisse et al., "Protein Expression in Mammalian and Insect Cell Systems", Methods in Enzymology, 1999, pp. 19-43, vol. 306.
Gentry et al., "Safety and efficiency of an anti-(+)-methamphetamine monoclonal antibody in the protection against cardiovascular and central nervous system effects of (+)-methamphetamine in rats", International Immunopharmacology, 2006, pp. 968-977, vol. 6.
Giudicelli et al., "IMGT/V-QUEST, an integrated software program for immunoglobulin and T cell receptor V—J and V—D—J rearrangement analysis", Nucleic Acid Res., 2004, pp. W435-W440, vol. 32.
Hardin et al., "Pharmacodynamics of a Monoclonal Antiphencyclidine Fab with Broad Selectivity for Phencyclidine-Like Drugs", J. Pharmacol. Exp. Therapeutics, 1998, pp. 1113-1122, vol. 285, No. 3.
Hardin et al., "A Single Dose of Monoclonal Anti-Phencyclidine IgG Offers Long-Term Reductions in Phencyclidine Behavioral Effects in Rats", J. Pharmacol. Exp. Therapeutics, 2002, pp. 119-126, vol. 302, No. 1.
International Search Report from International Patent Application No. PCT/US03/38384, dated Jul. 2, 2004, 1 page.
International Search Report and Written Opinion from related International Patent Application No. PCT/US07/071354, dated Mar. 10, 2008, 17 pgs.
International Search Report from International Patent Application No. PCT/US01/12899, dated Oct. 10, 2001, 4 pgs.
Kipriyanov et al., "Generation of Recombinant Antibodies", Molecular Biotechnology, 1999, pp. 173-201, vol. 12, No. 2.
Kosten et al., "Immunotherapy for the treatment of drug abuse", Pharmacology & Therapeutics, 2005, pp. 76-85, vol. 108.
Kunert et al., "Stable Recombinant Expression of the Anti HIV-1 Monoclonal Antibody 2F5 After IgG3/IgG1 Subclass Switch in CHO Cells", Biotechnol. and Bioeng., 2000, pp. 97-103, vol. 67, No. 1.
Kuus-Reichel et al., "Will Immunogenicity Limit the Use, Efficacy, and Future Development of Therapeutic Monoclonal Antibodies?", Clinical and Diagnostic Laboratory Immunology, 1994, pp. 365-372, vol. 1, No. 4.
Lacy et al., "Engineering and Characterization of a Mouse/Human Chimeric Anti-Phencyclidine Monoclonal Antibody", Int. Immunopharmacol., 2008, pp. 1-11, vol. 8, No. 1.
Laurenzana et al., "Use of Anti-(+)-Methamphetamine Monoclonal Antibody to Significantly Alter (+)Methamphetamine and (+)-Amphetamine Disposition in Rats," Drug Metabolism and Disposition, 2003, pp. 1320-1326, vol. 31, No. 11.
Laurenzana et al., "Treatment of Adverse Effects of Excessive Phencyclidine Exposure in Rats with a Minimal Dose of Monoclonal Antibody," J. Pharmacol. and Exp. Therap., 2003, pp. 1092-1098, vol. 306, No. 3.
Li et al., "Four-choice drug discrimination in pigeons," Behavioural Pharmacology, 2001, pp. 621-628, vol. 12, No. 8.
Lim et al., "Crystal Structure of Monoclonal 6B5 Fab Complexed with Phencyclidine," J. Bio. Chem., 1998, pp. 28576-28582, vol. 273, No. 44.
McCLURKAN et al., "Disposition of a Monoclonal Antiphencyclidine Fab Fragment of Immunoglobulin G in Rats," J. Pharmacology and Exp. Therap., 1993, pp. 1439-1445, vol. 266, No. 3.
International Search Report and Written Opinion from related International Application No. PCT/US14/25890, dated Oct. 6, 2014, 9 pgs.
Owens et al., "Mus musculus mAb3F2 immunoglobulin kappa light chain mRNA, partial cds", GenBank Accession No. DQ381545.1, dated Feb. 1, 2007, 2 pgs.
Wang et al., "Mus musculus anti-PRSV coat protein monoclonal antibody PRSV-H 10-9 immunoglobulin heavy chain variable region mRNA, complete cds", GenBank Accession No. AY571285.1, dated Jul. 21, 2004, 2 pgs.

* cited by examiner

SEQUENCE LISTING

<160> NUMBER OF SEQ ID NOS: 10

<210> SEQ ID NO 1
<211> LENGTH: 648
<212> TYPE: DNA
<213> ORGANISM: Artificial Sequence
<220> FEATURE:
<223> OTHER INFORMATION: SYNETHESIZED

<400> SEQUENCE: 1

```
caaatcgttc tcatccagtc tccaccaatc atgtctgcgt ctcctgggga gaaggtcacc      60
ttgacctgca gtgccagctc aagtgtaagt tccaggtact tgtactggta ccagcagaag     120
ccaggatcct cccccaaact ctggatttat ggcacatcta acctggcttc tggagtccct     180
gctcgcttca gtggcagtgg gtctgggacc tctttctctc tcacaatcag cagcatggag     240
gctgaagatg ctgcctctta tttctgccat cagtggagta gtttcccatt cacgttcggc     300
tcggggacaa agttggaaat aaaacgggct gatgctgcac caactgtatc catcttccca     360
ccatccagtg agcagttaac atctggaggt gcctcagtcg tgtgcttctt gaacaacttc     420 tacccaaag acatcaatgt caagtggaag attgatggca gtgaacgaca aaatggcgtc     480
ctgaacagtt ggactgatca ggacagcaaa gacagcacct acagcatgag cagcaccctc     540
acgttgacca aggacgagta tgaacgacat aacagctata cctgtgaggc cactcacaag     600
acatcaactt cacccattgt caagagcttc aacaggaatg agtgttag                  648
```

<210> SEQ ID NO 2
<211> LENGTH: 1326
<212> TYPE: DNA
<213> ORGANISM: Artificial Sequence
<220> FEATURE:
<223> OTHER INFORMATION: SYNTHESIZED

<400> SEQUENCE: 2

```
gagatccagc tgcaacagtc tggacctgag ctggggaagc ctggggcttc agtgaaggta      60
tcctgcaggg cttctggttt ctcattcgct gactactaca tttactgggt gaaacagagc     120
catggaaaga gccttgaatt gattggatat attgatcctt caatggtgg tgatacctat      180
aaccaaatat tcaagggcaa ggccacattg actgttgaca agtcctccag cacagccttc     240
atgtatctca cagcctgac atctgaagac tctgcagtct attactgtgc agcctttcgt      300
aacccttcct ttgacttctg gggccaaggc accactctca cagtccctc agccaaaacg      360
acacccccat ctgtctatcc actggcccct ggatctgctg cccaaactaa ctccatggtg     420
accctgggat gcctggtcaa gggctatttc cctgagccag tgacagtgac ctggaactct     480
ggatccctgt ccagcggtgt gcacaccttc ccagctgtcc tgcagtctga cctctacact     540
ctgagcagct cagtgactgt cccctccagc acctggccca gcgagaccgt cacctgcaac     600
gttgcccacc cggccagcag caccaaggtg gacaagaaaa ttgtgcccag ggattgtggt     660
tgtaagcctt gcatatgtac agtcccagaa gtatcatctg tcttcatctt ccccccaaag     720
cccaaggatg tgctcaccat tactctgact cctaaggtca cgtgtgttgt ggtagacatc     780
agcaaggatg atcccgaggt ccagttcagc tggtttgtag atgatgtgga ggtgcacaca     840
gctcagacgc aaccccggga ggagcagttc aacagcactt tccgctcagt cagtgaactt     900
cccatcatgc accaggactg gctcaatggc aaggagttca atgcagggt caacagtgca     960
gctttccctg cccccatcga gaaaaccatc tccaaaacca aggcagacc gaaggctcca    1020
caggtgtaca ccattccacc tcccaaggag cagatggcca aggataaagt cagtctgacc    1080
tgcatgataa cagacttctt ccctgaagac attactgtgg agtggcagtg gaatgggcag    1140
ccagcggaga actacaagaa cactcagccc atcatggaca cagatggctc ttacttcgtc    1200
tacagcaagc tcaatgtgca gaagagcaac tgggaggcag gaaatacttt cacctgctct    1260
gtgttacatg agggcctgca caaccaccat actgagaaga gcctctccca ctctcctggt    1320
aaatga                                                               1326
```

<210> SEQ ID NO 3
<211> LENGTH: 215
<212> TYPE: PRT
<213> ORGANISM: Artificial Sequence
<220> FEATURE:
<223> OTHER INFORMATION: SYTHENSIZED

<400> SEQUENCE: 3

```
Gln Ile Val Leu Ile Gln Ser Pro Pro Ile Met Ser Ala Ser Pro Gly
1               5                   10                  15

Glu Lys Val Thr Leu Thr Cys Ser Ala Ser Ser Val Ser Ser Arg
            20                  25                  30

Tyr Leu Tyr Trp Tyr Gln Gln Lys Pro Gly Ser Ser Pro Lys Leu Trp
        35                  40                  45

Ile Tyr Gly Thr Ser Asn Leu Ala Ser Gly Val Pro Ala Arg Phe Ser
    50                  55                  60

Gly Ser Gly Ser Gly Thr Ser Phe Ser Leu Thr Ile Ser Ser Met Glu
65                  70                  75                  80
```

Ala Glu Asp Ala Ala Ser Tyr Phe Cys His Gln Trp Ser Ser Phe Pro
                 85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
            195                 200                 205

Ser Phe Asn Arg Asn Glu Cys
            210                 215

<210> SEQ ID NO 4
<211> LENGTH: 441
<212> TYPE: PRT
<213> ORGANISM: Artificial Sequence
<220> FEATURE:
<223> OTHER INFORMATION: SYTHENSIZED

<400> SEQUENCE: 4

Glu Ile Gln Leu Gln Gln Ser Gly Pro Glu Leu Gly Lys Pro Gly Ala
1               5                   10                  15

Ser Val Lys Val Ser Cys Arg Ala Ser Gly Phe Ser Phe Ala Asp Tyr
            20                  25                  30

Tyr Ile Tyr Trp Val Lys Gln Ser His Gly Lys Ser Leu Glu Leu Ile
        35                  40                  45

Gly Tyr Ile Asp Pro Phe Asn Gly Asp Thr Tyr Asn Gln Ile Phe
    50                  55                  60

Lys Gly Lys Ala Thr Leu Thr Val Asp Lys Ser Ser Thr Ala Phe
65                  70                  75                  80

Met Tyr Leu Asn Ser Leu Thr Ser Glu Asp Ser Ala Val Tyr Tyr Cys
                85                  90                  95

Ala Ala Phe Arg Asn Pro Ser Asp Phe Trp Gly Gln Gly Thr Thr
            100                 105                 110

Leu Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
            130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
            195                 200                 205

Lys Val Asp Lys Lys Ile Val Pro Arg Asp Cys Gly Cys Lys Pro Cys
            210                 215                 220

-continued

```
Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
            245                 250                 255

Val Val Asp Ile Ser Lys Asp Pro Glu Val Gln Phe Ser Trp Phe
        260                 265                 270

Val Asp Asp Val Glu Val His Thr Ala Gln Thr Gln Pro Arg Glu Glu
    275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
    355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440
```

<210> SEQ ID NO 5
<211> LENGTH: 9
<212> TYPE: PRT
<213> ORGANISM: Artificial Sequence
<220> FEATURE:
<223> OTHER INFORMATION: SYTHENSIZED

<400> SEQUENCE: 5

```
Ser Ser Ser Val Ser Ser Arg Tyr Leu
1               5
```

<210> SEQ ID NO 6
<211> LENGTH: 11
<212> TYPE: PRT
<213> ORGANISM: Artificial Sequence
<220> FEATURE:
<223> OTHER INFORMATION: SYTHENSIZED

<400> SEQUENCE: 6

```
Tyr Gly Thr Ser Asn Leu Ala Ser Gly Val Pro
1               5                   10
```

<210> SEQ ID NO 7
<211> LENGTH: 9
<212> TYPE: PRT
<213> ORGANISM: Artificial Sequence
<220> FEATURE:
<223> OTHER INFORMATION: SYNTHESIZED

```
<400> SEQUENCE: 7

Cys His Gln Trp Ser Ser Phe Pro Phe
1               5

<210> SEQ ID NO 8
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 8

Ala Asp Tyr Tyr Ile Tyr
1               5

<210> SEQ ID NO 9
<211> LENGTH: 13
<212> TYPE: PRT
<213> ORGANISM: Artificial Sequence
<220> FEATURE:
<223> OTHER INFORMATION: SYNETHESIZED

<400> SEQUENCE: 9

Tyr Ile Asp Pro Phe Asn Gly Gly Asp Thr Tyr Asn Gln
1               5                   10

<210> SEQ ID NO 10
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 10

Tyr Tyr Cys Ala Ala Phe Arg Asn Pro
1               5
```

ANTI-(+)—METHAMPHETAMINE MONOCLONAL ANTIBODIES

GOVERNMENT SUPPORT

This invention was made with government support under grant numbers DA014361, DA011560 and GM103450 awarded by National Institutes of Health. The government has certain rights in the invention.

FIELD OF THE INVENTION

The invention relates to anti-(+) methamphetamine monoclonal antibodies and methods of using the antibodies to block or reduce methamphetamine-induced pharmacological effects.

BACKGROUND OF THE INVENTION

Methamphetamine abuse has been a significant problem in the United States for the last decade. According to the Substance Abuse and Mental Health Services Administration, there were 439,000 methamphetamine users in the U.S. in 2011. New methamphetamine users numbered 133,000. In 2010, more than 100,000 were admitted to drug abuse treatment with methamphetamine as their primary substance of abuse. In addition, there were 54.9 emergency department visits per 100,000 population aged 21 or older involving methamphetamine use.

Current treatments for methamphetamine abuse are generally not effective in the long term. The Center for Substance Abuse Treatment (CSAT) at UCLA reported that 36% of patients who successfully completed treatment programs used (+) methamphetamine again in the first 6 months after treatment and another 15% used again within 13 months (Brecht et al., 2000). Thus, at least half of patients completing treatment programs eventually used methamphetamine again. These high recidivism rates may occur because current approaches are primarily supportive. Although some symptoms of methamphetamine abuse and toxicity may be treated effectively (e.g., treating hypertension with antihypertensives, suppressing depression and anxiety of withdrawal with pharmacologic adjuncts), no treatments exist to reduce the pleasurable reinforcing effects of (+) methamphetamine use that promote addiction (i.e. the euphoric rush that drug users crave). The most effective current treatments for methamphetamine addiction are cognitive behavioral interventions—long-term approaches used to modify patient thinking, expectations, and behaviors and increase skills in coping with various life stressors while patients learn drug avoidance techniques.

Thus, the prior art lacks an effective pharmacological approach to reduce critical reinforcing effects of methamphetamine, as well as the means to effectively treat methamphetamine overdose. The present invention fulfills this long-standing need and desire in the art.

SUMMARY OF THE INVENTION

One aspect of the invention encompasses a method of effectively treating at least one clinically detectable symptom of methamphetamine use which comprises administering an effective amount of an anti-(+) methamphetamine antibody to a living human subject. In another aspect, the invention encompasses an antibody useful in such treatment. For instance, an antibody that therapeutically attenuates the toxic effects of methamphetamine in a living mammal or the effects of methamphetamine that promotes addiction in a living mammal.

Another aspect of the invention encompasses a composition comprising at least one anti-(+) methamphetamine antibody. In an aspect, the invention encompasses a composition comprising at least one anti-(+) methamphetamine antibody comprising a CDR selected from SEQ ID NOs: 5-10. In another aspect the composition comprises at least one anti-(+) methamphetamine antibody comprising a heavy chain of SEQ ID NO: 4 or a light chain of SEQ ID NO: 3. In yet another aspect, the invention encompasses a medicinal composition comprising at least one anti-(+) methamphetamine antibody. In still another aspect, the invention encompasses a medicinal composition comprising at least one anti-(+) methamphetamine antibody comprising a CDR selected from SEQ ID NOs: 5-10 or the heavy chain of SEQ ID NO: 4 or the light chain of SEQ ID NO: 3.

Some aspects of the invention encompass a medicinal composition useful to treat at least one clinically detectable symptom of methamphetamine use. The composition comprises a medicinally effective amount of an anti-(+) methamphetamine antibody, such as those described herein, adapted for administration to a living human subject. In an aspect, an antibody useful in such treatment includes an antibody that therapeutically attenuates the toxic effects of methamphetamine in a living mammal or the effects of methamphetamine that promote addiction in a living mammal. In an aspect, the medicinal composition is effectively administered to a living subject.

Other aspects of the invention encompass a medicinal kit comprising a container containing a functional therapeutic medicinal composition of a medicinally effective amount of an anti-(+) methamphetamine antibody adapted for administration to a living human subject and any medical devices to be used for said administration. In an aspect, an antibody useful in such treatment includes an antibody, such as those described herein, that therapeutically attenuates the toxic effects of methamphetamine in a living mammal or the effects of methamphetamine that promote addiction in a living mammal.

Other aspects and iterations of the invention are detailed below.

BRIEF DESCRIPTION OF THE FIGURES

The patent or application file contains at least one drawing executed in color. Copies of this patent or patent application publication with color drawing(s) will be provided by the Office upon request and payment of the necessary fee.

and (C) show distance traveled versus time. (B) and (D) show the area under the locomotor activity curves from 0-120 min (when significant stereotypic behavior and horizontal motion occurs), and from 120-240 min when the predominant response is horizontal motion (as measured by distance traveled). White/open circles (A and C) and bars (B and D) represent vehicle; black/closed circles (A and C) and bars (B and D) represent Antibody 51.

Figure 3:
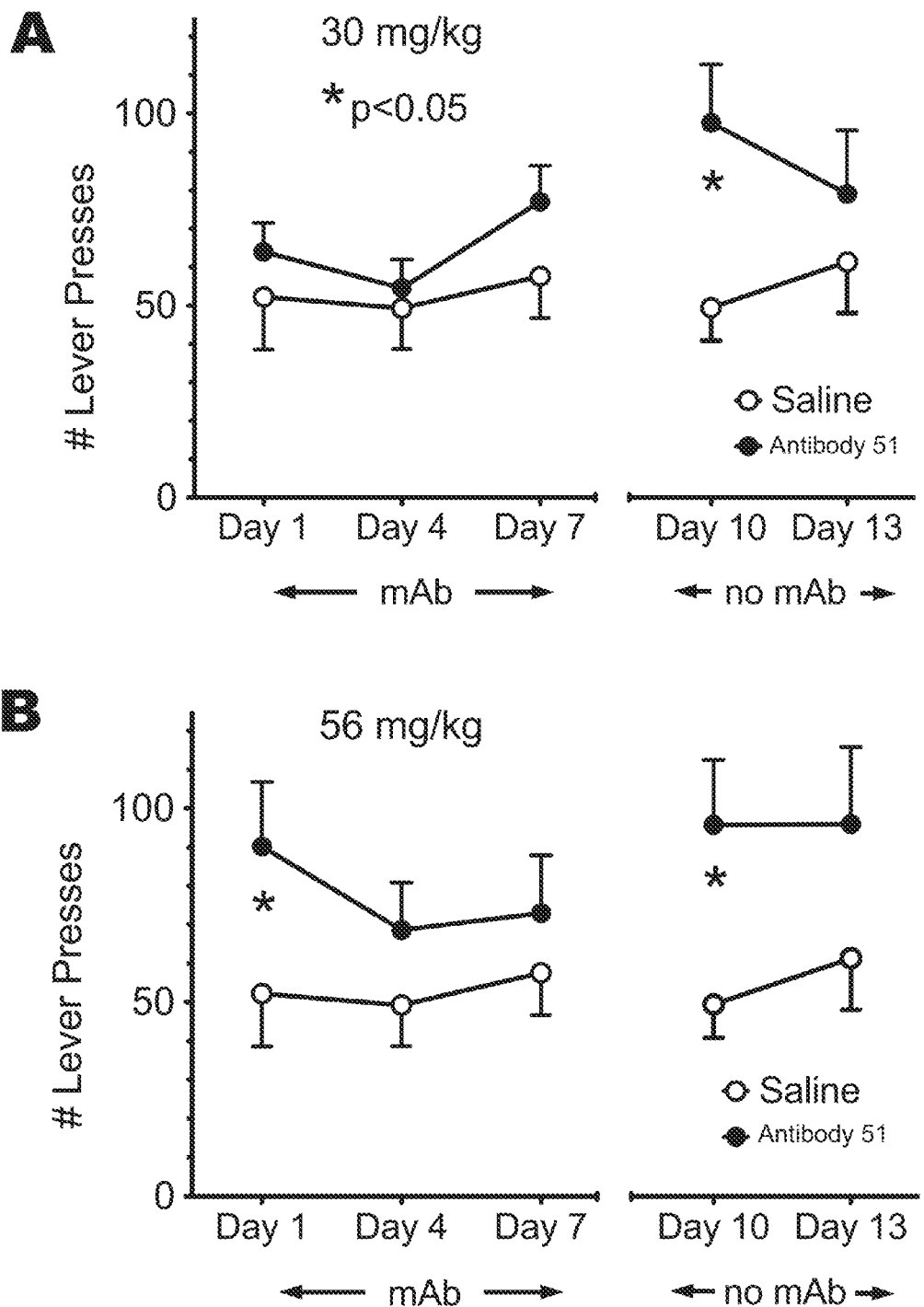
Figure 3C:
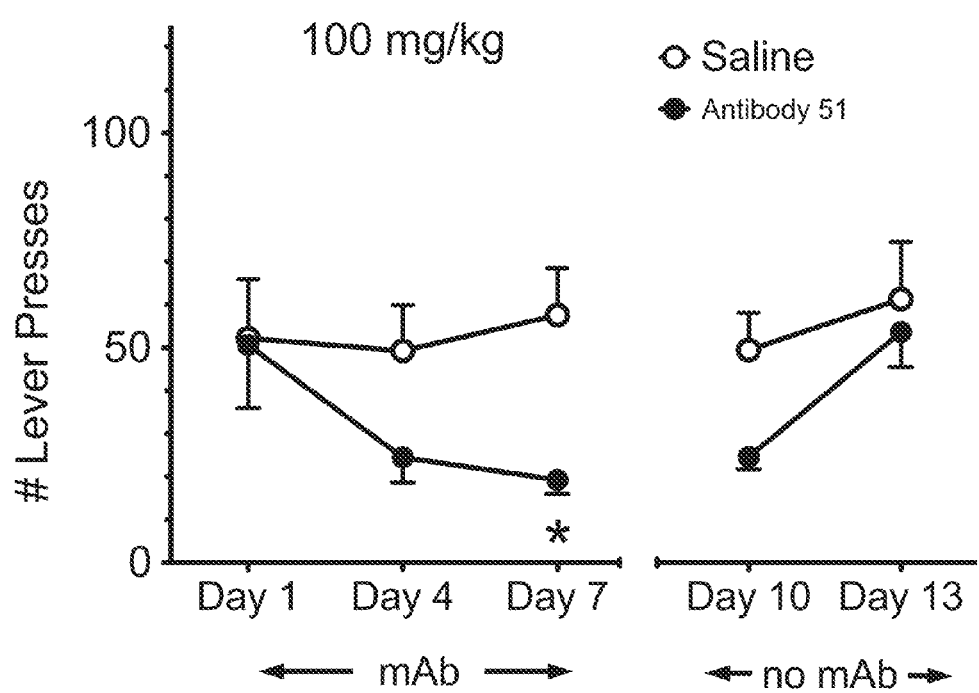
Figure 4:
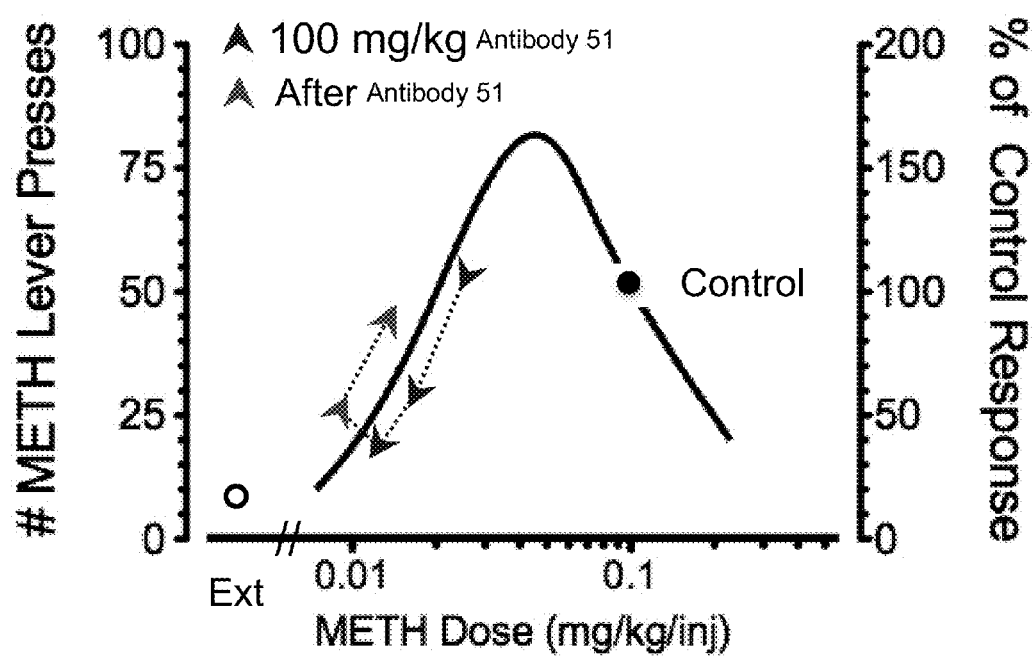

FIG. 3 depicts graphs showing the number of lever presses (y-axis) on Day 1, Day 4, Day 7, Day 10 and Day 13 (x-axis) for the saline group (open circles) and Antibody 51 group (closed circles) at three doses: 30 mg/kg (A), 56 mg/kg (B), and 100 mg/kg (C). Antibody or saline administration stopped on Day 10, hence Day 10 and Day 13 are identified as "no mAb". *$p<0.05$ FIG. 4 depicts a graph showing the number of METH lever presses (left y-axis) and % of control response (right y-axis) vs. METH injection dose (x-axis). Lever presses vs. (+)-METH dose is depicted as the solid black, bell-shaped curve. This theoretical bell shaped curve was generated from dose-response data from rats trained to lever press for different unit doses of METH from previous studies in our laboratory. The average percentage change in lever pressing on each day of Antibody 51 treatment as during (blue arrows beside the black line) and after mAb treatment (red arrows beside the black line) is plotted in combination with the previous obtained bell shaped METH-dose response curve. The direction of the connected arrowheads is an interpretation of time- and dose-progressive changes in responding in the presence of Antibody 51 down to levels that were near extinction levels of responding.

Figure 5:
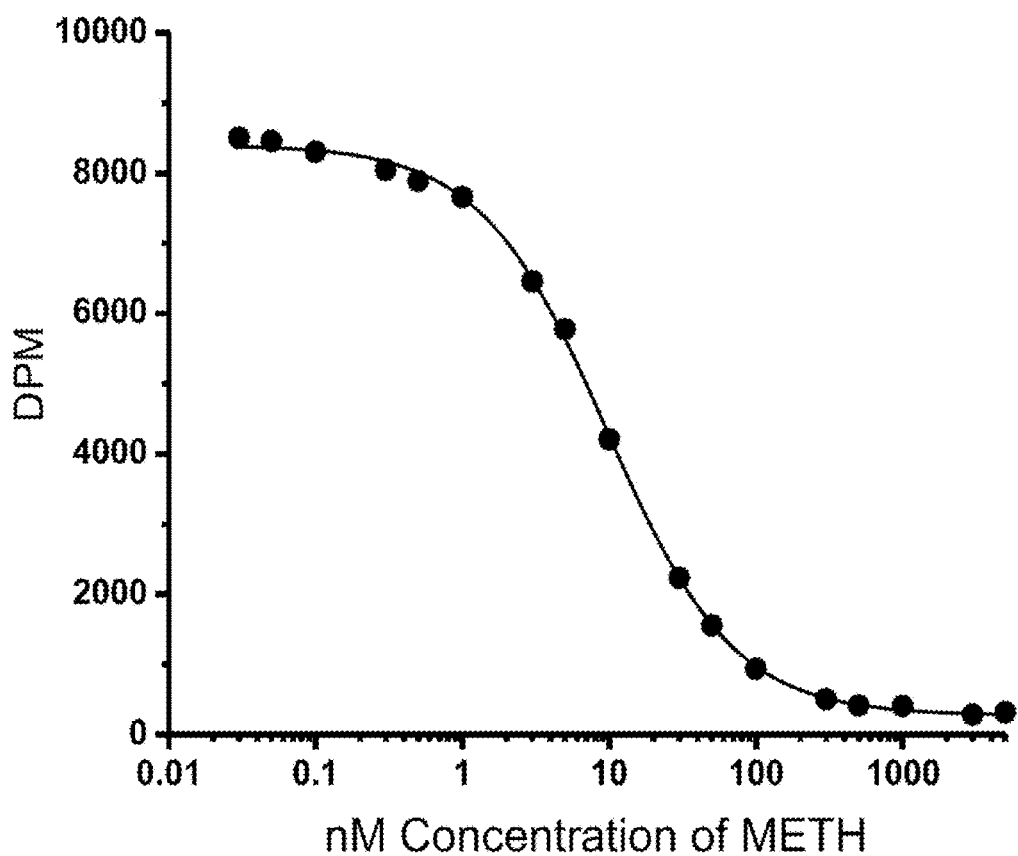

FIG. 5 depicts a graph showing a typical curve of DPM (decays per minute of the radioligand) vs. nM concentration of METH (or other test inhibitors) from a ligand cross-reactivity assay. These assays start with the incubation of radiolabeled METH (as a tracer ligand) with unlabeled METH or other ligand inhibitors over a range of concentrations. In this figure, the inhibitor is unlabeled METH, see x-axis for range of concentrations), ch-Antibody 51 is the METH binding antibody, and Protein G conjugated to magnetic beads is used to separate antibody bound METH from free METH. After reaching equilibrium, the beads are separated from the solution with a magnet. Antibody-bound [$^3$H]-METH is quantified by liquid scintillation counting and the DPM are graphed as a function of the unlabeled inhibitor concentration in the tube. The concentration of inhibitor required to inhibit [$^3$H]-METH binding by 50% minus the concentration of [$^3$H]-METH is the $K_D$ (if METH) or $K_I$ (if nonhomologous inhibitor) value.

DETAILED DESCRIPTION

The present invention provides anti-(+) methamphetamine antibodies and methods of use thereof for treating the medical problems associated with methamphetamine use. The antibodies of the present invention effectively block and/or reduce methamphetamine-induced pharmacological effects. Therefore, administering a pharmacologically effective amount of an antibody of the invention to a living subject in need thereof would provide suitable antagonism of methamphetamine pharmacokinetic properties. Hence, the present invention encompasses the discovery that an anti-(+) methamphetamine antibody provides a treatment for methamphetamine abuse and/or addiction, including acute and chronic overdose, and drug use relapse.

A. Medical Problems Associated with Methamphetamine Use

Methamphetamine occurs in two enantiomers, dextrorotary and levorotary. Dextromethamphetamine (or (+) methamphetamine) possesses the well-known psychostimulant effects of the drug, while levomethamphetamine is CNS-inactive. Illicitly, methamphetamine may be sold either as pure dextromethamphetamine or in a racemic mixture. As used herein, the terms "(+) methamphetamine" and "dextromethamphetamine" refer to a sample with only the dextrorotary enantiomer, while the term "methamphetamine" refers to a racemic mixture. However, when describing the pharmacological effects of methamphetamine (i.e. a racemic mixture), it is to be understood these properties are interchangeable with the properties of (+) methamphetamine since levomethamphetamine is CNS-inactive.

Methamphetamine has found use as both a medicinal and recreational drug. Methamphetamine can increase alertness, concentration, and energy in fatigued individuals in low doses. In higher doses, it can induce mania with accompanying euphoria, feelings of inflated self-esteem and increased libido. Methamphetamine has been approved by the Food and Drug Administration for the treatment of ADHD and exogenous obesity (obesity originating from factors outside of the patient's control) in both adults and children. It is also prescribed off-label for the treatment of narcolepsy and treatment-resistant depression. In the United States, methamphetamine is a Schedule II drug and is sold under the brand name Desoxyn. It is also synthesized and distributed illicitly.

In one aspect, the present invention encompasses anti-(+) methamphetamine antibodies and methods of use thereof for treating the medical problems associated with methamphetamine use. As used herein, the term "medical problems" refers to the adverse or toxic physical and/or psychological effects of methamphetamine use. The adverse or toxic physical and/or psychological effects of methamphetamine use are well known in the art. Non-limiting examples of the physical effects of methamphetamine use may include anorexia, hyperactivity, dilated pupils, flushed skin, excessive sweating, restlessness, dry mouth and bruxism (leading to "meth mouth"), headache, accelerated heartbeat, slowed heartbeat, irregular heartbeat, rapid breathing, high blood pressure, low blood pressure, high body temperature, diarrhea, constipation, blurred vision, dizziness, twitching, insomnia, numbness, palpitations, tremors, dry and/or itchy skin, acne, pallor, and—with chronic and/or high doses—convulsions, heart attack, stroke, and death. Non-limiting examples of psychological effects of methamphetamine use may include euphoria, anxiety, increased libido, alertness, concentration, increased energy, increased self-esteem, self-confidence, sociability, irritability, aggressiveness, psychosomatic disorders, psychomotor agitation, dermatillomania (compulsive skin picking), hair pulling, delusions of grandiosity, hallucinations, excessive feelings of power and invincibility, repetitive and obsessive behaviors, paranoia, and—with chronic use and/or high doses—amphetamine psychosis. In some exemplary embodiments, a medical problem associated with methamphetamine use may be methamphetamine abuse. In other exemplary embodiments, a medical problem associated with methamphetamine use may be methamphetamine addiction. In still other exemplary embodiments, a medical problem associated with methamphetamine use is the adverse or toxic effects of methamphetamine.

Further by "medical problems associated with methamphetamine use" is meant the reinforcing effects of methamphetamine that contribute to addiction and drug use relapse. The rapid onset of methamphetamine's subjective effects when smoked or injected intravenously is a factor in the reinforcing and addictive power of the drug. Methods of measuring the subjective effects of methamphetamine (e.g. euphoria, feeling "high", and craving) are known in the art. In some embodiments, a medical problem associated with methamphetamine use is the reinforcing effects of methamphetamine.

In another aspect, the present invention encompasses anti-(+) methamphetamine antibodies and methods of use thereof for treating medical problems associated with methamphetamine abuse and/or addiction. Methamphetamine has a high potential for abuse and addiction, activating the psychological reward system by triggering a cascading release of dopamine in the brain. The signs and/or symptoms of methamphetamine abuse and/or addiction are well known in the art, including but not limited to the physical and psychological effects of methamphetamine use described above, as well as the withdrawal and neurotoxic symptoms described below. Withdrawal symptoms of methamphetamine primarily consist of fatigue, depression, and increased appetite. Symptoms may last for days with occasional use and weeks or months with chronic use, with severity dependent on the length of time and the amount of methamphetamine used. Withdrawal symptoms may also include anxiety, irritability, headaches, agitation, restlessness, excessive sleeping, vivid or lucid dreams, deep REM sleep, and suicidal ideation. Methamphetamine use also has a high association with depression and suicide as well as serious heart disease, amphetamine psychosis, anxiety, and violent behaviors. Methamphetamine is not directly neurotoxic but long-term use can have neurotoxic side-effects. Its use is associated with an increased risk of Parkinson-like effects likely due to the fact that uncontrolled dopamine release is neurotoxic. Long-term dopamine upregulation occurring as a result of methamphetamine abuse can cause neurotoxicity, which is believed to be responsible for causing persisting cognitive deficits, such as memory loss, impaired attention, and decreased executive function. Similar to the neurotoxic effects on the dopamine system, methamphetamine can also result in neurotoxicity to the serotonin system.

In some embodiments, a medical problem associated with methamphetamine abuse may be acute methamphetamine overdose. In other embodiments, a medical problem associated with methamphetamine abuse may be chronic methamphetamine overdose. In still other embodiments, a medical problem associated with methamphetamine abuse may be the adverse effects of methamphetamine. In still other embodiments, a medical problem associated with methamphetamine abuse may be the toxic effects of methamphetamine. In yet other embodiments, a medical problem associated with methamphetamine abuse may be the reinforcing effects of methamphetamine. In different embodiments, a medical problem associated with methamphetamine abuse may be drug use relapse. In alternative embodiments, a medical problem associated with methamphetamine abuse may be the risk of drug dependence in populations who have not yet become drug dependent.

B. Anti-(+) Methamphetamine Antibodies

According to the invention, anti-(+) methamphetamine antibodies useful herein include all antibodies that therapeutically attenuate the medical problems associated with methamphetamine use. The medical problems associated with methamphetamine use are described in detail above.

Useful antibodies include, but are not limited to, those that specifically bind to a unique epitope within (+) methamphetamine, or that specifically bind to a common epitope within (+) methamphetamine, (+) methamphetamine metabolites, (+) methamphetamine-like stimulants, or a combination thereof. Non-limiting examples of (+) methamphetamine metabolites include (+) amphetamine. (+) Methamphetamine-like stimulants refers to structurally related stimulants and/or hallucinogenic analogs. Non-limiting examples, (+) methamphetamine-like analogs include (+) 3,4-methylenedioxymethamphetamine (MDMA) and (+) 3,4-methylenedioxyamphetamine (MDA).

In an aspect, antibodies useful herein include those antibodies which have been isolated, characterized, purified, are functional and have been recovered (obtained) for use in a functional therapeutic composition which is administered to a living subject having signs or symptoms of methamphetamine use, methamphetamine abuse and/or methamphetamine addiction. Signs or symptoms of methamphetamine use, methamphetamine abuse and/or methamphetamine addiction are described in detail above.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. Bispecific monoclonal antibodies (i.e. a protein that comprises fragments of two different monoclonal antibodies and consequently binds two different antigens) are also included within the definition of "antibody". As long as the protein retains the ability specifically to bind its intended target, it is included within the term "antibody." Also included within the definition "antibody" for example are single chain forms, generally designated Fv (or scFV for single chain fragment variable), regions, of antibodies with this specificity. Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred for some applications. Antibodies are properly cross-linked via disulfide bonds, as is known.

The basic antibody structural unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Anti-(+) methamphetamine antibodies useful herein include those which are isolated, characterized, purified, functional and have been recovered (obtained) from a process for their preparation and thus available for use herein in a useful form in a therapeutically and medicinally sufficient amount.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-(+) methamphetamine antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a hapten as described in U.S. Pat. No. 7,202,348, incorporated by reference in its entirety. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-(+) methamphetamine antibody that is composed partially or fully of amino acid sequences derived from a human antibody by altering, combining, or replacing sequences with those from an antibody having non-human CDRs. The simplest such alteration may consist of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for (+) methamphetamine is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems (e.g. at least the B cells) have been altered to correspond to those of the human immune system. As mentioned above, it is sufficient for use in the methods of this discovery, to employ an immunologically specific fragment of the antibody, including fragments representing single chain forms.

Further, as used herein the term "humanized antibody" refers to an anti-(+) methamphetamine antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, ct al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the invention specifically binds (+) methamphetamine, and may also bind a metabolite of (+) methamphetamine, or a (+) methamphetamine-like stimulant. The phrase "specifically binds" herein means antibodies bind to the (+) methamphetamine, or a metabolite of (+) methamphetamine, with a binding constant in the range of at least $10^{-4}$-$10^{-6}$ $M^{-1}$, with a preferred range being $10^{-7}$-$10^{-9}$ $M^{-1}$. Methods of determining whether an antibody binds to (+) methamphetamine, a metabolite of (+) methamphetamine, or a (+) methamphetamine-like stimulant are known in the art, and are further detailed in the Examples. In some embodiments, the specific antibodies may recognize (+) methamphetamine. In other embodiments, the specific antibodies may recognize two compounds from the group consisting of (+) methamphetamine, (+) amphetamine, and (+) MDMA. In an exemplary embodiment, the specific antibodies may recognize all three compounds of the group consisting of (+) methamphetamine, (+) amphetamine, and (+) MDMA. In another exemplary embodiment, the specific antibodies may recognize all three compounds of the group consisting of (+) methamphetamine, (+) amphetamine, and (+) MDMA, and not recognize (−) methamphetamine, (−) amphetamine, and (−) MDMA. In still another exemplary embodiment, the specific antibodies may recognize all three compounds of the group consisting of (+) methamphetamine, (+) amphetamine, and (+) MDMA, and not recognize over the counter medications.

A preferred antibody is a humanized form of a mouse antibody comprising a CDR selected from SEQ ID NOs:

5-10. Stated another way, a "preferred antibody" comprises at least one CDR region comprised of the amino acid sequence selected from the group consisting of SEQ ID NO: 5, 6, 7, 8, 9, and 10.

In one embodiment, an antibody of the invention may be encoded by a nucleic acid sequence comprising 90, 91, 92, 93, 94, 95, 96, 97, 98, or 99% identity to the light chain variable region of SEQ ID NO:1, or may be encoded by a nucleic acid sequence comprising 90, 91, 92, 93, 94, 95, 96, 97, 98, or 99% identity to the heavy chain variable region of SEQ ID NO:2. In another embodiment, an antibody of the invention may comprise an amino acid sequence with 90, 91, 92, 93, 94, 95, 96, 97, 98, or 99% identity to the light chain variable region of SEQ ID NO:3, or may comprise an amino acid sequence with 90, 91, 92, 93, 94, 95, 96, 97, 98, or 99% identity to the heavy chain variable region of SEQ ID NO:4. In each of the above embodiments, the antibody may be humanized.

In an exemplary embodiment of an antibody of the invention that binds to (+) methamphetamine, the antibody comprises the light chain nucleic acid sequence of SEQ ID NO:1 and the heavy chain nucleic acid sequence of SEQ ID NO:2. In another exemplary embodiment of an antibody of the invention that binds to (+) methamphetamine, the antibody comprises the light chain amino acid sequence of SEQ ID NO:3 and the heavy chain amino acid sequence of SEQ ID NO:4.

In one embodiment, an antibody of the invention may comprise a light chain CDR1, such as the antibody 1 of Table A. In another embodiment, an antibody of the invention may comprise a light chain CDR2, such as the antibody 4 Table A. In yet another embodiment, an antibody of the invention may comprise a light chain CDR3, such as the antibody 6 Table A. In an alternative embodiment, an antibody of the invention may comprise a combination of two or three light chain CDRs, such as the antibodies 2, 3, and 5 of Table A.

Similarly, in one embodiment, an antibody of the invention may comprise a heavy chain CDR1, such as the antibody 7 of Table A. In another embodiment, an antibody of the invention may comprise a heavy chain CDR2, such as the antibody 10 of Table A. In yet another embodiment, an antibody of the invention may comprise a heavy chain CDR3, such as the antibody 12 of Table A. In an alternative embodiment, an antibody of the invention may comprise a combination of two or three heavy chain CDRs, such as the antibodies 8, 9, and 11 of Table A.

Alternatively, an antibody of the invention may comprise one or more light chain CDRs and one or more heavy chain CDRs, such as the antibodies 13-48 of Table A.

TABLE A

| Antibody | Light Chain | | | Heavy Chain | | |
|---|---|---|---|---|---|---|
| | CDR1 | CDR2 | CDR3 | CDR1 | CDR2 | CDR3 |
| 1 | SEQ ID NO: 5 | | | | | |
| 2 | SEQ ID NO: 5 | SEQ ID NO: 6 | | | | |
| 3 | SEQ ID NO: 5 | SEQ ID NO: 6 | SEQ ID NO: 7 | | | |
| 4 | | SEQ ID NO: 6 | | | | |
| 5 | | SEQ ID NO: 6 | SEQ ID NO: 7 | | | |
| 6 | | | SEQ ID NO: 7 | | | |
| 7 | | | | SEQ ID NO: 8 | | |
| 8 | | | | SEQ ID NO: 8 | SEQ ID NO: 9 | |
| 9 | | | | SEQ ID NO: 8 | SEQ ID NO: 9 | SEQ ID NO: 10 |
| 10 | | | | | SEQ ID NO: 9 | |
| 11 | | | | | SEQ ID NO: 9 | SEQ ID NO: 10 |
| 12 | | | | | | SEQ ID NO: 10 |
| 13 | SEQ ID NO: 5 | | | SEQ ID NO: 8 | | |
| 14 | SEQ ID NO: 5 | | | SEQ ID NO: 8 | SEQ ID NO: 9 | |
| 15 | SEQ ID NO: 5 | | | SEQ ID NO: 8 | SEQ ID NO: 9 | SEQ ID NO: 10 |
| 16 | SEQ ID NO: 5 | | | | SEQ ID NO: 9 | |
| 17 | SEQ ID NO: 5 | | | | SEQ ID NO: 9 | SEQ ID NO: 10 |
| 18 | SEQ ID NO: 5 | | | | | SEQ ID NO: 10 |
| 19 | SEQ ID NO: 5 | SEQ ID NO: 6 | | SEQ ID NO: 8 | | |
| 20 | SEQ ID NO: 5 | SEQ ID NO: 6 | | SEQ ID NO: 8 | SEQ ID NO: 9 | |
| 21 | SEQ ID NO: 5 | SEQ ID NO: 6 | | SEQ ID NO: 8 | SEQ ID NO: 9 | SEQ ID NO: 10 |
| 22 | SEQ ID NO: 5 | SEQ ID NO: 6 | | | SEQ ID NO: 9 | |
| 23 | SEQ ID NO: 5 | SEQ ID NO: 6 | | | SEQ ID NO: 9 | SEQ ID NO: 10 |
| 24 | SEQ ID NO: 5 | SEQ ID NO: 6 | | | | SEQ ID NO: 10 |
| 25 | SEQ ID NO: 5 | SEQ ID NO: 6 | SEQ ID NO: 7 | SEQ ID NO: 8 | | |
| 26 | SEQ ID NO: 5 | SEQ ID NO: 6 | SEQ ID NO: 7 | SEQ ID NO: 8 | SEQ ID NO: 9 | |
| 27 | SEQ ID NO: 5 | SEQ ID NO: 6 | SEQ ID NO: 7 | SEQ ID NO: 8 | SEQ ID NO: 9 | SEQ ID NO: 10 |
| 28 | SEQ ID NO: 5 | SEQ ID NO: 6 | SEQ ID NO: 7 | | SEQ ID NO: 9 | |
| 29 | SEQ ID NO: 5 | SEQ ID NO: 6 | SEQ ID NO: 7 | | SEQ ID NO: 9 | SEQ ID NO: 10 |
| 30 | SEQ ID NO: 5 | SEQ ID NO: 6 | SEQ ID NO: 7 | | | SEQ ID NO: 10 |
| 31 | | SEQ ID NO: 6 | | SEQ ID NO: 8 | | |
| 32 | | SEQ ID NO: 6 | | SEQ ID NO: 8 | SEQ ID NO: 9 | |
| 33 | | SEQ ID NO: 6 | | SEQ ID NO: 8 | SEQ ID NO: 9 | SEQ ID NO: 10 |
| 34 | | SEQ ID NO: 6 | | | SEQ ID NO: 9 | |
| 35 | | SEQ ID NO: 6 | | | SEQ ID NO: 9 | SEQ ID NO: 10 |
| 36 | | SEQ ID NO: 6 | | | | SEQ ID NO: 10 |
| 37 | | SEQ ID NO: 6 | SEQ ID NO: 7 | SEQ ID NO: 8 | | |
| 38 | | SEQ ID NO: 6 | SEQ ID NO: 7 | SEQ ID NO: 8 | SEQ ID NO: 9 | |
| 39 | | SEQ ID NO: 6 | SEQ ID NO: 7 | SEQ ID NO: 8 | SEQ ID NO: 9 | SEQ ID NO: 10 |
| 40 | | SEQ ID NO: 6 | SEQ ID NO: 7 | | SEQ ID NO: 9 | |
| 41 | | SEQ ID NO: 6 | SEQ ID NO: 7 | | SEQ ID NO: 9 | SEQ ID NO: 10 |
| 42 | | SEQ ID NO: 6 | SEQ ID NO: 7 | | | SEQ ID NO: 10 |
| 43 | | | SEQ ID NO: 7 | SEQ ID NO: 8 | | |
| 44 | | | SEQ ID NO: 7 | SEQ ID NO: 8 | SEQ ID NO: 9 | |
| 45 | | | SEQ ID NO: 7 | SEQ ID NO: 8 | SEQ ID NO: 9 | SEQ ID NO: 10 |

TABLE A-continued

| Anti-body | Light Chain | | | Heavy Chain | | |
|---|---|---|---|---|---|---|
| | CDR1 | CDR2 | CDR3 | CDR1 | CDR2 | CDR3 |
| 46 | | | SEQ ID NO: 7 | | SEQ ID NO: 9 | |
| 47 | | | SEQ ID NO: 7 | | SEQ ID NO: 9 | SEQ ID NO: 10 |
| 48 | | | SEQ ID NO: 7 | | | SEQ ID NO: 10 |

TABLE B

| Anti-body | Light Chain | Heavy Chain |
|---|---|---|
| 49 | SEQ ID NO: 3 | |
| 50 | | SEQ ID NO: 4 |
| 51 | SEQ ID NO: 3 | SEQ ID NO: 4 |

In various embodiments, an antibody of the invention is humanized. For instance, in one embodiment, a humanized antibody of the invention may comprise a light chain variable region comprising a CDR1 of amino acid sequence SEQ ID NO: 5 with zero to two amino acid substitutions, a CDR2 of amino acid sequence SEQ ID NO: 6 with zero to two amino acid substitutions, and a CDR3 of amino acid sequence SEQ ID NO: 7, or may comprise a heavy chain variable region comprising a CDR1 of amino acid sequence SEQ ID NO: 8 with zero to two amino acid substitutions, a CDR2 of amino acid sequence SEQ ID NO: 9 with zero to two amino acid substitutions, and a CDR3 of amino acid sequence SEQ ID NO:10 with zero to two amino acid substitutions. In a preferred embodiment, a humanized antibody of the invention may comprise a light chain variable region comprising a CDR1 of amino acid sequence SEQ ID NO:5 with zero to two amino acid substitutions, a CDR2 of amino acid sequence SEQ ID NO:6 with zero to two amino acid substitutions, a CDR3 of amino acid sequence SEQ ID NO:7, a heavy chain variable region comprising a CDR1 of amino acid sequence SEQ ID NO:8 with zero to two amino acid substitutions, a CDR2 of amino acid sequence SEQ ID NO:9 with zero to two amino acid substitutions, and a CDR3 of amino acid sequence SEQ ID NO:10 with zero to two amino acid substitutions. In an exemplary embodiment, a humanized antibody of the invention may comprise a light chain variable region comprising a CDR1 of amino acid sequence SEQ ID NO:5, a CDR2 of amino acid sequence SEQ ID NO:6, a CDR3 of amino acid sequence SEQ ID NO:7, a heavy chain variable region comprising a CDR1 of amino acid sequence SEQ ID NO:8, a CDR2 of amino acid sequence SEQ ID NO:9, and a CDR3 of amino acid sequence SEQ ID NO:10. The invention also encompasses the corresponding nucleic acid sequences of SEQ ID NO:5, 6, 7, 8, 9, and 10, which can readily be determined by one of skill in the art, and may be incorporated into a vector or other large DNA molecule, such as a chromosome, in order to express an antibody of the invention.

In an aspect, the antibodies in a pharmacologically effective amount preferred in pharmaceutical grade, including immunologically reactive fragments, are administered to a subject such as to a living subject to be treated for methamphetamine abuse associated symptoms. Administration is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living subject. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl) propyl]-N,N,N-trimethyl ammonium chloride (DOTMA) or various compounds such as cholesterol hemisuccinate, phosphatidyl glycerols and the like.

The concentration of humanized antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living subject could be made up to contain 1 mL sterile buffered water of phosphate buffered saline and about 1-1500 mg of any one of or a combination of the humanized antibody of the present discovery. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-(+) methamphetamine antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immunoglobulins, IgM antibodies tend to have greater activity loss than IgG antibodies). Dosages administered are effective dosages and may have to be adjusted to compensate. The pH of the formulations, generally of pharmaceutical grade quality, will be selected to balance antibody stability (chemical and physical) and comfort to the subject when administered. Generally, a pH between 4 and 8 is tolerated. Doses will vary from individual to individual based on size, weight, and other physiobiological characteristics of the individual receiving the successful administration.

As used herein, the term "effective amount" means an amount of a substance such as a compound that leads to measurable and beneficial effects for the subject administered the substance, i.e., significant efficacy. The effective amount or dose of compound administered according to this discovery will be determined by the circumstances surrounding the case, including the compound administered, the route of administration, the status of the symptoms being treated and similar subject and administration situation considerations among other considerations. In an aspect, a typical dose contains from about 0.01 mg/kg to about 100 mg/kg of an anti-(+) methamphetamine antibody described herein. Doses can range from about 0.05 mg/kg to about 50 mg/kg, more preferably from about 0.1 mg/kg to about 25 mg/kg. The frequency of dosing may be daily or once, twice, three times or more per week or per month, as needed as to effectively treat the symptoms. In exemplary embodiments, the frequency of dosing can range from once a week to once a month, more preferably once every two to four weeks. For example, the frequency of dosing may be once a week, once every two weeks, once every three weeks, or once every four weeks.

The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outsubject clinic. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

C. Methods of Using Anti-(+) Methamphetamine Antibodies

In another aspect, an anti-(+) methamphetamine antibody of the invention is admixed with at least one suitable compatible adjuvant or excipient resulting in a therapeutic medicinal composition which is capably and effectively administered (given) to a living subject afflicted with signs or symptoms of methamphetamine use, abuse and/or addiction. Typically this is an aqueous composition of high purity. Suitable anti-(+) methamphetamine antibodies are described above in Section IB. Non-limiting examples of suitable subjects include a human or a lab animal. In some embodiments, the subject is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In other embodiments, the subject is a human.

As used herein, the terms "treating" or "treatment" include prevention, attenuation, reversal, or improvement in at least one symptom or sign of methamphetamine use, abuse or addiction. Signs or symptoms of methamphetamine use, abuse and addiction are described in detail above in Section IA.

As used herein the term "therapeutically attenuate" includes inducing a change or having a beneficial positive effect resulting therefrom.

In one embodiment, the invention provides a method for treating at least one medical problem associated with methamphetamine use in a subject. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above.

In another embodiment, the invention provides a method for treating at least one medical problem associated with methamphetamine abuse in a subject. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. Methods of diagnosing methamphetamine abuse are known in the art.

In another embodiment, the invention provides a method for treating at least one medical problem associated with methamphetamine addiction in a subject. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. Methods of diagnosing methamphetamine addiction are known in the art.

In another embodiment, the invention provides a method for treating at least one toxic effect associated with methamphetamine use in a subject. The method comprises administering a therapeutically effective amount of an antibody that specifically binds to (+) methamphetamine to the subject. Suitable antibodies include those disclosed herein. Non-limiting examples of toxic effects are also disclosed herein. In some exemplary embodiments, a suitable antibody comprises an antibody delineated in Table A above. In other exemplary embodiments, the toxic effect may be selected from the group consisting of convulsions, heart attack, stroke, toxicity, and neurotoxicity.

In another embodiment, the invention provides a method for treating at least one adverse effect associated with methamphetamine use in a subject. The method comprises administering a therapeutically effective amount of an antibody that specifically binds to (+) methamphetamine to the subject. Suitable antibodies include those disclosed herein. Non-limiting examples of adverse effects are also disclosed herein. In some exemplary embodiments, a suitable antibody comprises an antibody delineated in Table A above. In other exemplary embodiments, the adverse effect may be selected from the group consisting of anxiety, hallucinations, amphetamine psychosis, and paranoia.

In another embodiment, the invention provides a method for treating acute methamphetamine overdose in a subject addicted to methamphetamine. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. Methods of diagnosing acute methamphetamine overdose are known in the art.

In another embodiment, the invention provides a method for treating chronic methamphetamine overdose in a subject addicted to methamphetamine. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. Methods of diagnosing chronic methamphetamine overdose are known in the art.

In another embodiment, the invention provides a method for preventing relapse in methamphetamine use in a subject addicted to methamphetamine. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above.

In another embodiment, the invention provides a method for reducing the frequency of relapse in methamphetamine use in a subject addicted to methamphetamine. "Frequency of relapse", as used herein, may refer to the chances that a subject will return to abuse of methamphetamine after an initial period of recovery. The initial period of recovery can and will vary without limitation over a time period of one or more days to a time period ranging from a week to several years. Frequency of relapse may be measured against control or treatment subjects and may be used to describe individuals or groups in comparison to untreated or negative control treated subjects. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. The frequency of relapse may be decreased by at least 1, 2, 3, 4, 5, 6, 7, 8, 9, 10, 11, 12, 13, 14, 15, 16, 17, 18, 19, or 20% compared to untreated or negative control treated subjects. In some embodiments, the frequency of relapse may be decreased by at least 20, 25, 30, 35, 40, 45, 50, 55, 60, 65, 70, 75, 80, 85, 90, or 95% compared to untreated or negative control treated subjects. In other embodiments, the frequency of relapse may be decreased by at least 100, 125, 150, 200, 250, 300, 350, 400, or 450% compared to untreated or negative control treated subjects. Methods of measuring the frequency of relapse are known in the art.

In another embodiment, the invention provides a method for reducing the risk of drug dependence in populations who have not yet become drug dependent but are at risk. "At risk" populations may include, but is not limited to, fetuses and nursing infants of drug abusing mothers, and adolescent children who are not yet using drugs but have drug-dependent parents. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above.

In another embodiment, the invention provides a method for slowing the rate of (+) methamphetamine entry into the brain of a subject in a subject. Stated differently, the rate of (+) methamphetamine entry into the brain is slower or reduced in comparison to the rate of (+) methamphetamine entry into the brain without treatment. The method comprises administering a therapeutically effective amount of an antibody that specifically binds to (+) methamphetamine to the subject. Suitable antibodies include those disclosed herein. In exemplary embodiments, a suitable antibody comprises an antibody delineated in Table A above. Methods of measuring the rate of (+) methamphetamine entry into the brain of a subject are known in the art. For example, (+) methamphetamine concentrations in brain tissue, cerebral spinal fluid, or interstitial fluid may be measured over time.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense.

EXAMPLES

The following examples illustrate various iterations of the invention.

Example 1

Production of Mouse Anti-METH Monoclonal Antibodies

METH-like hapten (S)-(+)-3-(9-carboxynonyloxy)methamphetamine (abbreviated (+)-METH M010) (Peterson E C et al. *J Pharmacol Exp Ther* (2007) 322: 30-39; Carroll F I et al. *Med Chem* (2009) 52, 7301-7309) was covalently bound to bovine serum albumin (BSA) using a carbodiimide coupling procedure (Davis M T and Preston J F *Anal Biochem* (1981) 116: 402-407). This synthesis involves formation of a covalent bond between the carboxylic acid terminus on the METH (+)MO10 hapten and the terminal amino acid groups on BSA. The (+)-METH MO10 hapten to BSA epitope density of the final product (5:1) was determined by mass spectrometry.

For discovery of anti-METH monoclonal antibody secreting hybridoma cell lines, the following general technique was used. Groups of female BALB/c mice were immunized with the METH (+)MO10-BSA conjugate (e.g., 20 μg of antigen), emulsified in an equal volume of Freund's Complete adjuvant. Three weeks and eight weeks later the mice were boosted with the same METH conjugate vaccine and adjuvant. Two weeks later the mouse sera were tested for METH specific antibodies using a (+)-METH MO10-ovalbumin conjugate in an ELISA format, and the response was judged high enough for production of monoclonal antibodies. The spleen from the animal with the highest titer of anti-METH antiserum was used for this process. The hybridoma fusion partner for the mouse spleen cells was myeloma cell line P3×63Ag8.653 (American Type Culture Collection, Manassas, Va.). After the successful fusion, hybridomas secreting anti-METH antibodies were identified using an ELISA, with a METH (+)MO10-ovalbumin conjugate as previously described (Laurenzana E M et al. *Drug Metab Dispos* (1995) 23: 271-278).

IgG isotype and light chain identity was determined with a mouse antibody isotyping kit (Roche Diagnostics, Indianapolis, Ind.). Micro titer plate wells with a positive reaction to METH were subcloned to monoclonality. Anti-METH IgG antibodies were chosen from several of the most promising clones in tissue culture. In subsequent testing, the Ig isotype, IgG light chain type, antibody ligand specificity, affinity for METH-like drugs, and cell line IgG production levels (a critical factor for the eventual use in large scale IgG production) were determined. Once the best candidate mAbs were identified, more extensive characterization of specificity with a series of ligands was conducted using radioimmunoassay with a [$^3$H]-METH radioligand. A master and working cell bank was created from these stabilized monocloanl antibody hybrimdoma cells lines. All cell lines were then stored in liquid nitrogen.

Example 2

Determination of Long-Term In Vivo Function of a Murine Anti(+)-METH Antibody

The in vivo binding function of the three anti-METH mAbs (Antibody 51, mAb10D1, and mAb4G9) over time after mAb treatment was assessed by comparing the effects of the pre-mAb (for average (+)-METH serum steady state concentrations) and post-mAb on the serum pharmacokinetics of METH, and the area under the METH serum concentration time curve from day 0 through day 13. Day 0 of the study started one day after implantation of the sc (+)-METH osmotic pumps. The dosing groups are shown in Table 1.

TABLE 1

MAb long-term function Groups

| Study Group | Treatment | Challenge dosing | Rat # |
|---|---|---|---|
| 1 | mAb4G9 180 mg/kg | 2-week sc infusion of 5.6 mg/kg (+)-METH | 2 |
| 2 | Antibody 51 180 mg/kg | 2-week sc infusion of 5.6 mg/kg (+)-METH | 4 |
| 3 | mAb10D1 180 mg/kg | 2-week sc infusion of 5.6 mg/kg (+)-METH | 2 |
| | | Total | 8 |

The mAbs were formulated just prior to the rat studies. All procedures were performed in a safety hood in a protein purification clean room. Purification of the anti-mAbs was achieved by affinity chromatography with a protein G-Sepharose column (GE Healthcare, Chalfont St. Giles, Buckinghamshire, UK) (Peterson et al. *J Pharmacol Exp Ther* (2007) 322(1): 30-39). After purification, the mAbs were concentrated on a 500 ml stirred cell (Amicon Inc., Beverly, Mass.) with a 30,000 molecular weight cutoff cellulose membrane (Millipore Corporation, Bedford, Mass.). The buffer was exchanged in the same process to 15 mM sodium phosphate containing 150 mM sodium chloride (pH 6.5-7.5). To assure that endotoxin concentrations in the final protein solutions were insignificant, a Limulus Amebocyte Lysate kit (QCL-1000; Cambrex Corp., East Rutherford, N.J.) was used to assay the final product. The endotoxin levels were insignificant. Final antibody product was ultracentrifuged at 100,000×g for 90 min at 4° C. to remove possible large molecular weight antibody complexes, which can be highly antigenic. UV absorbance and SDS-polyacrylamide gel electrophoresis were conducted to determine protein concentrations and to ensure purity of the final preparation, respectively. To prepare the mAb doses, an aliquot of stock antibody solution was centrifuged at ~100,000 times gravity for 1 hr at 4° C. The supernatant was stored in a sterile sealed vial at 4° C. until dose preparation. Prior administration to rats, purified mAb was quickly warmed to 37° C. before drawing the doses into sterile syringes.

For these studies, rats (n=2 per controls and mAb test groups) with dual jugular vein catheters were housed individually in standard cages. Osmotic minipumps (2 weeks, Alzet, Durect Corp., Cupertino, Calif.) were prepared to deliver a (+)-METH (free base) dose of 5.6 mg/kg/day dissolved in sterile saline. The pumps were implanted subcutaneously between the scapulae of rats while under halothane anesthesia.

About 16 h after pumps implantation, the rats were anesthetized with halothane. Blood samples (~250 μl) were immediately collected via the right jugular vein catheters for determination of pre-mAb-METH serum steady-state levels. The catheter was flushed with 200 μl sterile saline. A mAb dose (180 mg/kg, the same dose for all three mAbs in this study) equimolar in binding sites to the body burden of METH at the time of dosing was then administered via the left jugular vein catheter. Following the mAb dose, the catheter was flushed with 200 μl of saline. At 5 min after the mAb administration, a blood sample was collected via right jugular vein catheter. Blood samples (~350 μl) were collected via the right jugular catheter at 24 hr, 4, 7, and 13 days after mAb administration. On day 13, rats were anesthetized with halothane and sacrificed by decapitation. Trunk blood and brain samples were immediately collected. After allowing blood to clot, serum was collected by centrifugation. Serum samples were stored at −80° C. until analysis. METH concentrations in serum samples were then determined by liquid chromatograph/mass spectrometry/mass spectrometry (LC/MS/MS) analysis by a previously reported method from our laboratory (Laurenzana E M et al. *Drug Metab Dispos* (1995) 23: 271-278).

The route of (+)-METH dosing was a subcutaneous (sc) infusion. The treatments with saline, mAb control, and mAb test articles were through iv dosing via an indwelling catheter. This was a single dose administered 24 hrs after the start of the sc (+)-METH infusion. Body weights, eating behavior, and general health observations were recorded for each animal. (+)-METH concentrations were determined by LC/MS/MS, similar to the method described by described by (Laurenzana E M et al. *Drug Metab Dispos* (1995) 23: 271-278).

To determine the serum pharmacokinetic parameters of individual anti-METH mAbs, the average concentration-vs-time curves for mAb were analyzed by model-independent pharmacokinetic methods. For the METH serum data in the presence of various mAb, the area under the METH serum concentration-time curve (AUC) from time of mAb administration until the end of the study (Day 13; $AUC_{Day\ 0}^{Day\ 13}$) were determined using the linear trapezoidal rule and Origin Graphing and Analysis software version 7.0 (OriginLab Corp., Northampton, Mass.).

No significant changes in body weight, food consumption, medical conditions or unexpected behavioral changes were noted in the animals that completed the studies.

Figure 1:
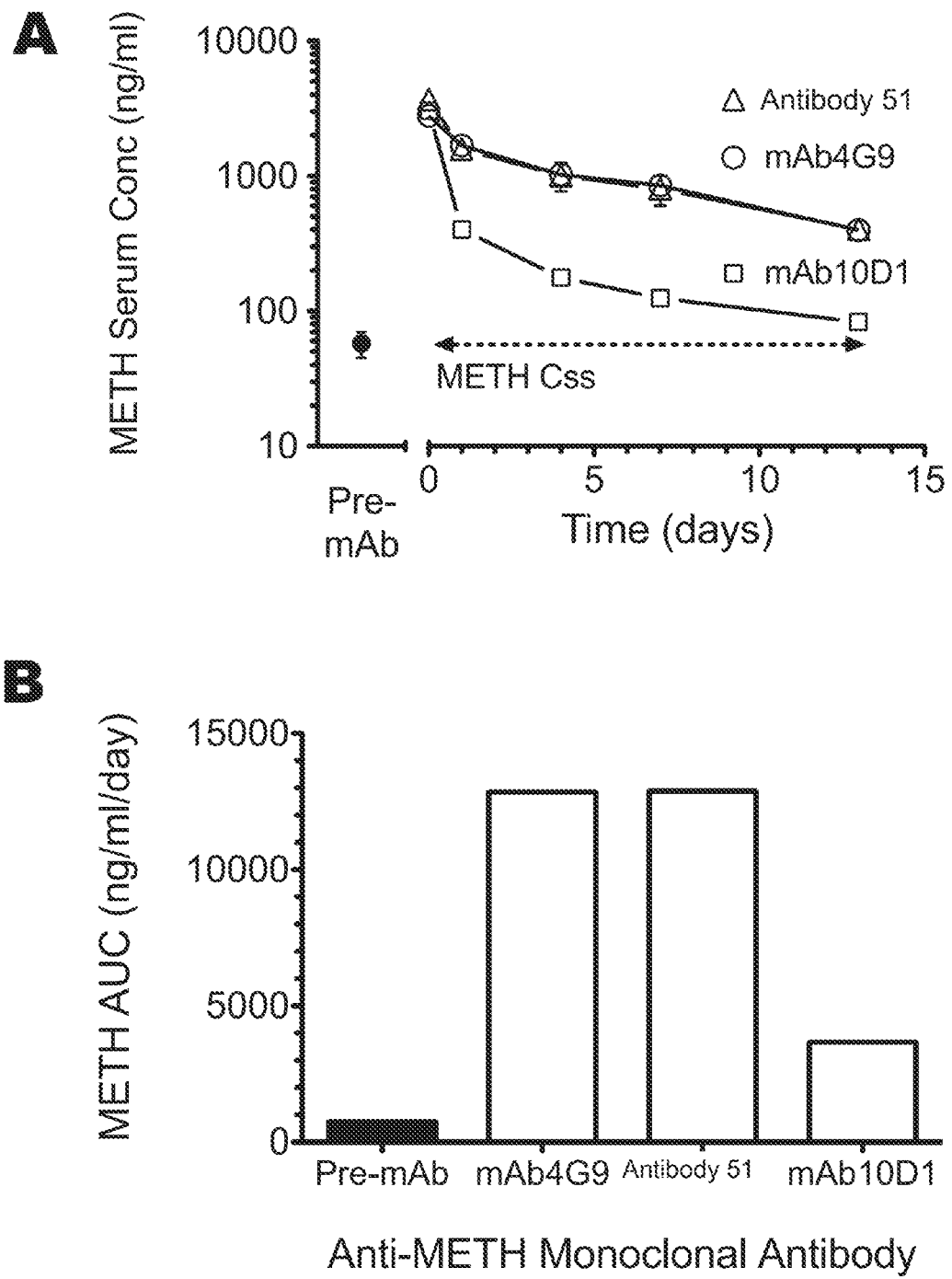
FIG. 1 depicts two graphs showing changes in METH in vivo binding by anti-METH monoclonal antibodies (mAbs) in the presence of a 13 day continuous METH infusion. Once METH achieved steady-state levels (pre-mAb) in each of the Sprague-Dawley rats (n=2 per group), a single dose of vehicle treatment (METH only) or of treatment with three different anti-METH mAbs were given as an iv bolus (180 mg/kg, equimolar in binding sites to the METH body burden). Serum samples were collected before the mAb treatment and at various time points after mAb treatment for determination of METH concentrations over time (A). Values represent the mean METH concentration of each group for each time point. METH AUC data is shown in (B).
Figure 2:
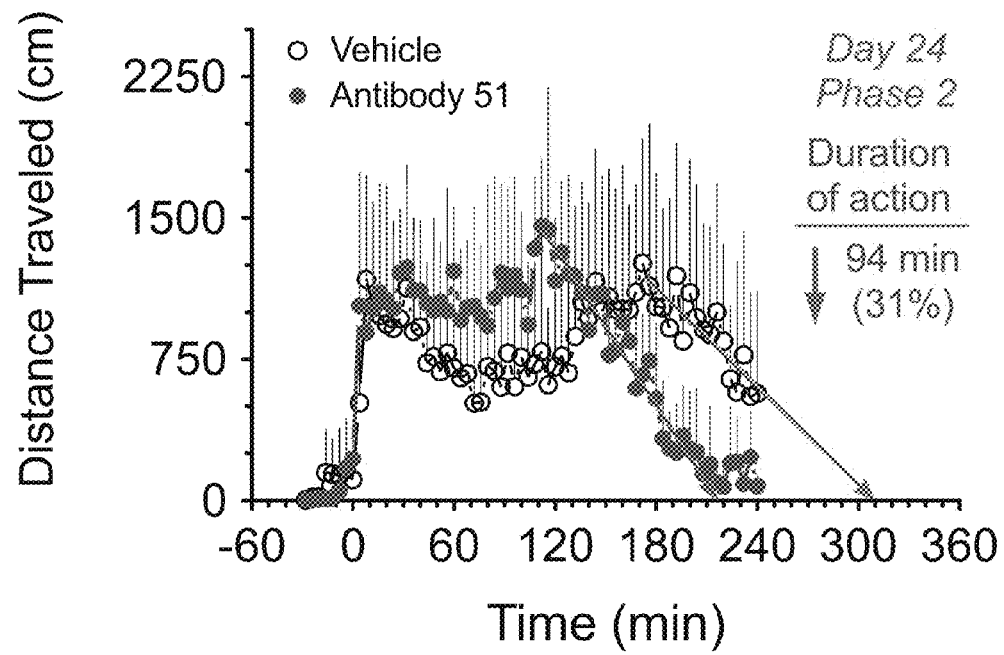
FIG. 2 depicts graphs showing locomotor activity following a 1.68 mg/kg dose of (+)-METH in phase 2 studies. These doses were administered 10 days A and B and 14 days (C and D) after the last Antibody 51 administration on day 14. (A)
Figure 2:
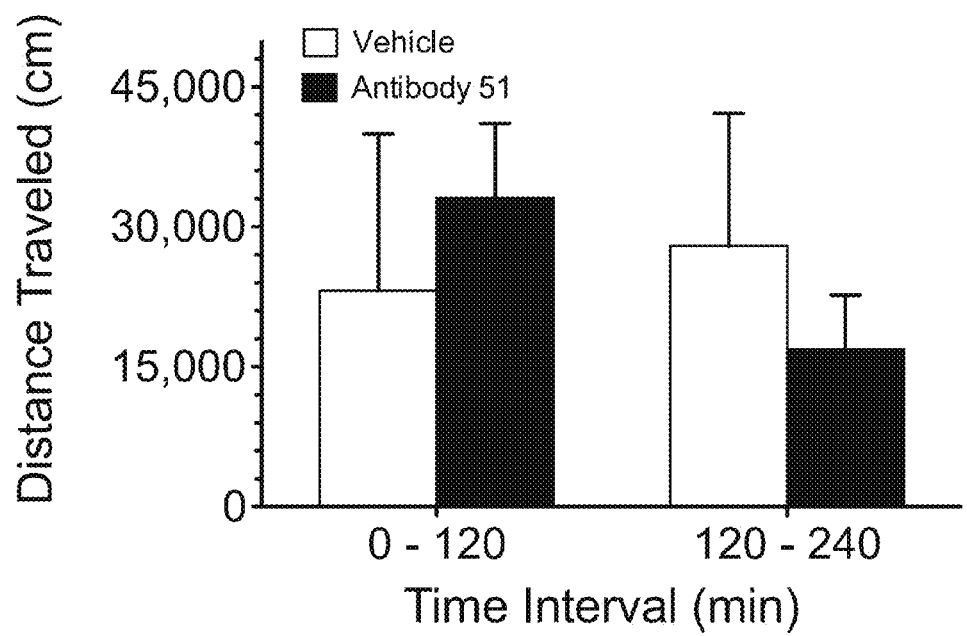
Figure 2:
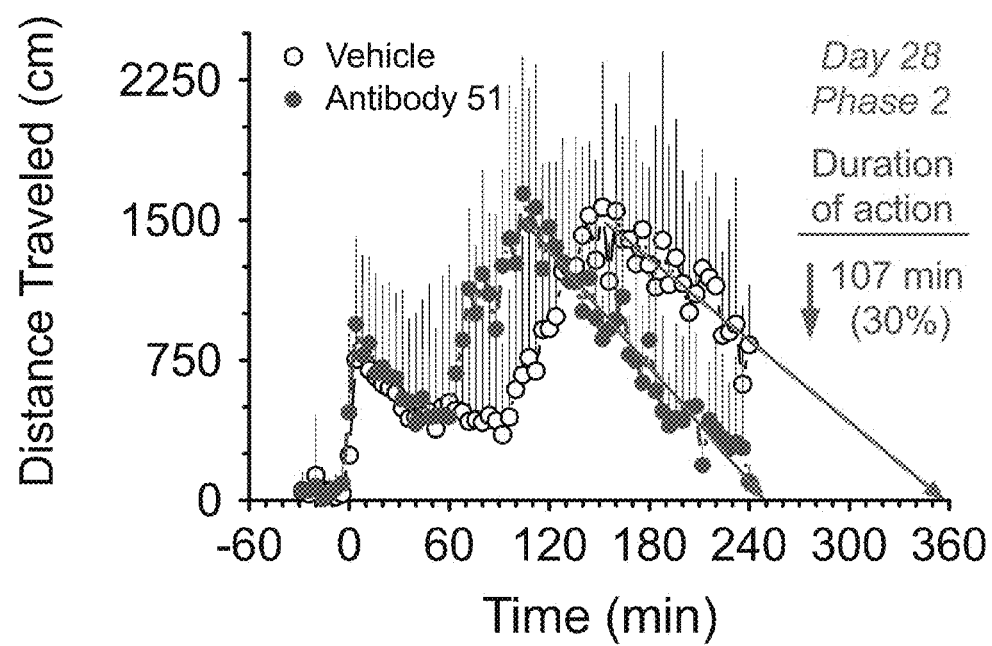
Figure 2:
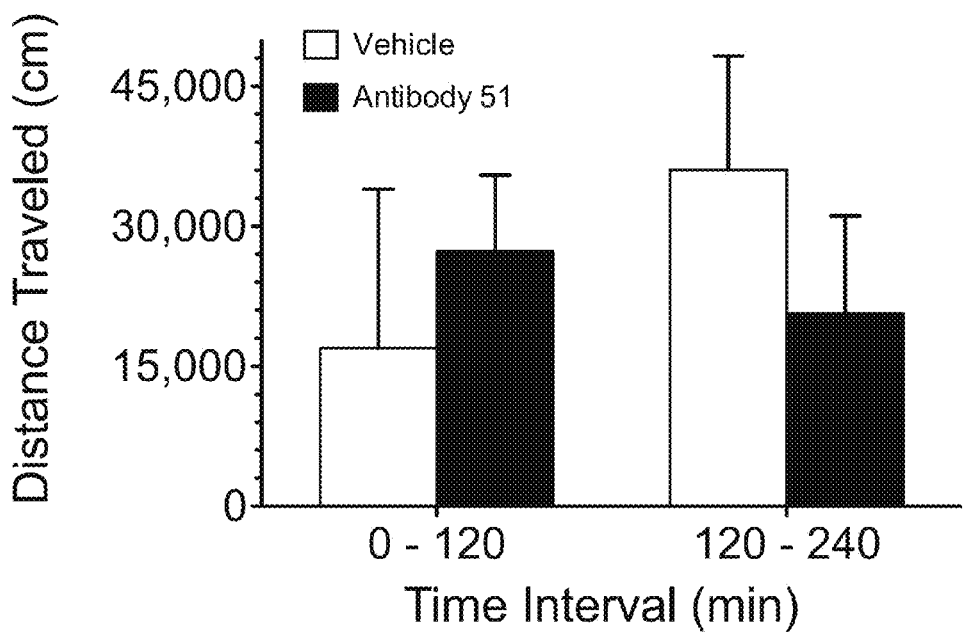

Antibody 51 (designated as mAb7F9 on the figures) showed long-term functional properties as previously reported for mAb4G9 (see FIG. 1; Owens S M et al. CNS Neurol Disord Drug Targets (2011) 10: 892-898; also see Laurenzana E M et al. *Drug Metab Dispos* (1995) 23: 271-278). Mab7F9 was rerun in this study as a positive control. MAb10D1 (METH KD=34 nM) did not show long-term function. More recent unpublished studies show that four of five mAbs generated from the same longer spacer arm hapten as mAb4G9 and Antibody 51 also have prolonged duration of action. Whereas four out five mAbs generated from a shorter METH-like hapten linker group showed inactivation after only 1-3 days in vivo (Laurenzana E M et al. *Drug Metab Dispos* (1995) 23: 271-278). Recent studies (unpublished) of a prototype antibody that is inactivated show mAb KD is not changed, but the capacity for METH binding (Bmax) is significantly reduced. This other antibody (mAb6H4) was generated through immunization with a METH-like hapten coupled to through a shorter linker group bound to an antigen protein carrier. This means there is a much smaller number of functioning antibodies once inactivation occurs. Thus we hypothesize a longer spacer arm between the METH backbone structure and the antigen is somehow protective against in vivo inactivation. We also know from these unpublished recent studies that the mAbs are inactivated in vivo with or without a (+)-METH infusion. This METH metabolite binding to the antibody binding site is a not part of the mechanism of inactivation.

In summary, this study demonstrates the importance of both in vitro and in vivo characterization of the functional properties of therapeutic mAbs. These data also suggest careful structure-activity studies with mAbs generated from a range of haptens can reveal better choices for optimal vaccines. The studies also show mAb in vivo function is not always predicted from in vitro immunochemical characterization. These results emphasize the need for extensive preclinical characterization of mAb therapeutics, and highlight the prolonged in vivo METH-binding function and efficacy of anti-METH mAb4G9 and Antibody 51.

Example 3

Prevention of METH-Induced Relapse in Rats

Antibody 51 was formulated as described in Example 2.

The male Long Evans rat was chosen as the animal model for this study because it is a preferred rodent species for preclinical toxicity testing of drug self-administration paradigms. Commercially obtained test chambers equipped with two retractable levers, a white cue light positioned above each lever, a 5-w house light, and a Sonalert® tone generator (MED Associates, Inc., St. Albans, Vt.) emitting a 2900 Hz, 60 dB tone were used. Infusions were delivered in a 0.2 ml volume by a 6-s activation of infusion pumps (Model PHS-100; MED Associates, Inc., St. Albans, Vt.). Recordings of lever presses and activations of lights, pumps, and Sonalerts® were accomplished by a microcomputer, interface and associated software (MED-PC® IV, MED Associates, Inc., St. Albans, Vt.).

(±)-METH self-administration (SA) training sessions were conducted five days per week (M-F) for 2 hrs daily. At the start of (±)-METH SA sessions, the levers were extended and the house light was illuminated. Each response (fixed ratio 1, FR1) on the right-side lever (reinforced-lever) resulted in delivery of a 0.1 mg/kg methamphetamine infusion (0.2 ml/6 s) followed by an additional 14-s timeout period. At the start of an infusion the house light was extinguished, the Sonalert® was sounded, and the cue lights above each lever flashed at 3 Hz. The Sonalert® and cue lights remained activated during the 6 s infusion. Twenty seconds following the onset of the infusion the house light was re-illuminated, and the opportunity to self-administer (±)-METH was again made available (i.e., each (±)-METH infusion initiated a 20 s period during which lever presses were recorded but were without scheduled consequences and further infusions could not be obtained). Reinforced-lever (right-side) lever presses during the infusions as well as all non-reinforced (left-side) lever presses were recorded, but the latter were without scheduled consequences.

SA training continued until all three criteria had been met: 1) at least 12 self-administration sessions occurred; 2) at least 15 (±)-METH infusions occurred during each of the last four sessions; and, 3) at least 125 lifetime (±)-METH infusions were obtained. Subsequently, twelve 2-h daily (Mon-Sun) extinction sessions were conducted. During extinction sessions, lever pressing did not result in infusions or stimulus changes, which were previously associated with (±)-METH infusions (i.e., neither offset of the house light, nor activation of cue lights and the Sonalert® occurred). Other conditions during extinction were identical to those during SA. That is, during extinction sessions, both levers were extended and the house light was activated. Before the last four extinction sessions, an injection of saline (the vehicle for (±)-METH prime) was administered ip 30 min pre-session to acclimate the rats to the injection procedure.

Reinstatement testing followed extinction training. A rat was considered eligible for subsequent reinstatement testing if during the last three extinction sessions the mean number of reinforced-lever lever presses was less than the mean number occurring during the first three extinction sessions. Rats that did not meet this extinction criterion were excluded from subsequent testing. One rat in the vehicle group was inadvertently retained, even though its response mean (12.3 responses) during the last three extinction sessions exceeded its first three extinction sessions (11.6 responses). Reinstatement testing occurred across 13 daily (Mon-Sun) 2-h experimental sessions. Conditions during reinstatement testing were identical to those during extinction training with two exceptions. 1) Either saline (S) or 1 mg/kg (±)-METH (M) (i.e., (±)-METH prime) was administered ip 30 min pre-session according to the following daily schedule: MSSMSSMSSMSSM, and 2) six hours before the start of the first (Day 1), second (Day 4), and third (Day 7) (±)-METH test sessions either a dose of Antibody 51 or 0.9% sterile saline (for the vehicle test Group) was administered iv through the catheters. For prolonged effects of mAb treatment on (±)-METH priming-induced reinstatement, no Antibody 51 (or saline vehicle) was given for the last two (±)-METH test sessions (Day 10 and Day 13). Groups of 12 rats were randomly assigned to each of the four METH priming-induced reinstatement test groups: 1) Antibody 51 vehicle (saline); 2) 30 mg/kg Antibody 51; 3) 56 mg/kg Antibody 51; 4) 100 mg/kg Antibody 51 (see Table 3).

TABLE 3

Behavioral Study Groups

| Study Group | Treatment | Challenge dosing | Rat # |
| --- | --- | --- | --- |
| 1 | Vehicle | Saline | 12 |
| 2 | Antibody 51 30 mg/kg | (±)-METH 1 mg/kg | 12 |
| 3 | Antibody 51 56 mg/kg | (±)-METH 1 mg/kg | 12 |
| 4 | Antibody 51 100 mg/kg | (±)-METH 1 mg/kg | 12 |
| | | Total | 60 |

The ip route of (±)-METH exposure during relapse testing was selected mainly for convenience of dosing and to avoid additional use of the catheters. The test article (Antibody 51) was administered via iv catheter infusion (over approximately 2 min) once on Day 1, Day 4 and Day 7. The dose volume for each animal was based on the most recent body weight measurement.

Body weights, eating behavior, and general health observations were recorded for each animal. Analyses of an animal's lever pressing responses to vehicle and (±)-METH-induced relapse to active lever responding were used as a measure of the animal's response to an ip injection of vehicle (control) or (±)-METH (1.0 mg/kg).

Initially, the number of right-side lever presses occurring during test days between test groups was compared using a two-factor, repeated measures ANOVA (Prism 5 for Macintosh, GraphPad Software, Inc., San Diego, Calif.). If results with the ANOVA were found significant (p<0.05), comparisons between similar test days between the two test groups were conducted using a Bonferroni Test (Prism 5 for Macintosh, GraphPad Software, Inc., San Diego, Calif.). Comparisons were considered statistically significant if p<0.05.

Numbers of lever presses on the reinforced lever during the last day of SA did not differ significantly (p>0.61) amongst all test groups, indicating that all rats had been trained to self-administer (±)-METH to similar levels prior to extinction training. During extinction sessions immediately preceding each relapse test session, numbers of lever presses on the reinforced lever also did not differ significantly amongst test groups (p>0.2), indicating that the rats had been extinguished to similar levels prior to each reinstatement test. However, when examining these numbers among extinction sessions, the ANOVA was significant (p<0.04), although none of the Bonferroni pair-wise comparisons were significant, indicating that extinction levels did not systematically change with time (data not shown). (±)-METH primes significantly reinstated responding in the saline group during the Day 1, Day 4, Day 7, Day 10 and Day 13 (p<0.05) relapse test sessions, respectively, indicating these conditions were effective in generating METH-prime induced reinstatement regardless of time of testing.

When subjecting all data sets for each relapse test day to a Grubb's outlier test, there were three outliers in the control data and two in the 30 mg/kg Antibody 51 group. These data points were removed from the statistical analysis. The occurrence of outliers appeared random with no individual animals showing a pattern of generating repeated outliers. These five individual data points were from a total of 240 individual observations (5 days of testing, 12 animal per group, 4 control or Antibody 51 groups, 5×12×4=240 data points).

FIG. 5 shows results for lever presses on the reinforced lever for each relapse test for the control group (open circle) and all three doses of Antibody 51 (closed circles). The same results for the saline group (open circles) are repeated in each of the three graphs.

In the highest mAb treatment group (100 mg/kg Antibody 51, FIG. 5C), responding appeared to be at the same level as vehicle treatment responding during Day 1 testing, but then steadily declined from Day 4 to Day 7. By Day 7 (following the third Antibody 51 dose), responding was significantly reduced (p<0.05), compared to control responding. Responding remained blunted during Day 10 when Antibody 51 administration was stopped (p>0.08). By Day 13 it appeared to return to near control levels of responding. However, this apparent return to control levels of responding could be misleading, since responding in the 30 and 56 mg/kg groups remained elevated above vehicle baseline values at this same time point (FIGS. 5A and 5B).

In contrast, studies of 30 and 56 mg/kg doses (FIGS. 5A and 5B), showed response rates increased to 70 and 91 presses, or a 143% and 182% increase over control values on Day 1, respectively. Subsequent Antibody 51 treatments every three days with 30 and 56 mg/kg produced progressively lower responses from the Day 1 level of responding for the 56 mg/kg mAb dose, whereas the 30 mg/kg treatment maintained responding at levels always higher than the control.

To better understand the meaning of these mAb-induced changes, a pharmacodynamic analysis of the 100 mg/kg Antibody 51 was conducted (FIG. 5C). A graph was simulated showing the number of METH injections (y-axis) vs. METH injection dose (x-axis) plot. Data for this pharmacodynamic simulation were based on the (+)-METH SA studies of McMillan et al. (2004) conducted at UAMS. The simulation of SA data (lever presses vs. (+)-METH dose) is depicted as the solid black, bell-shaped curve in FIG. 6. As part of the interpretation, the average percentage change in lever pressing on each day of Antibody 51 treatment was plotted as during (blue arrows beside the black line) and after mAb treatment (red arrows beside the black line). The direction of the connected arrowheads is the interpretation of time- and dose-progressive changes in responding in the presence of Antibody 51.

This pharmacodynamic analysis indicated that Antibody 51 produced dramatic changes in the perceived or apparent effects of the (±)-METH-priming dose. Thus on Day 1, when there was no apparent difference between control and 100 mg/kg Antibody 51-treated levels of responding, the simulation suggests that the Antibody 51 treated rats actually had ~50 lever presses on the ascending slope of the dose response curve, whereas in the current studies the saline-treated control values had ~50 lever presses on the descending slope of the dose response curve. This control data point is plotted as the solid black circle at 0.1 mg/kg/inj on the descending portion of the bell shaped dose-response curve in FIG. 6. Antibody 51-induced changes were in a time- and mAb dose-dependent manner. Indeed, each new mAb dose was accompanied by progressive shifts to the left along this bell-shaped curve, until the 3rd 100 mg/kg dose of Antibody 51 produced effects in rats that lead to a near extinction ("Ext", open black circle) level of responding.

This analysis shows that the apparent lack of change in response on Day 1 for the 100 mg/kg dose was not likely at "~50 responses" on the descending, right side of the bell-shaped curve at the same place as the "Control" value (FIG. 6, closed black circle), but on the ascending, left side of the dose-response curve where 50 responses intersect with a dose of ~0.025 mg/kg/inj (top blue arrowhead). Importantly, the next two 100 mg/kg mAb doses resulted in further substantive reductions in responding compared to control values. Thus, rats appeared to "perceive" the (±)-METH priming dose as much smaller than rats not treated with mAb. Although most addicted patients are expected to try at first to surmount neuroprotective effects of mAb dosing, these data suggest that under optimal conditions they will get little or no reinforcing effects.

These data from three different Antibody 51 doses also suggest the need for chronic Antibody 51 dosing to achieve maximal effects, even if the first doses appears to provide only partial or incomplete antagonism of METH effects. The need for repeated dosing to steady state is novel for mAb treatment of addiction, but totally consistent with the well-established clinical pharmacological principle that states maximum therapeutic benefit is not achieved until a patient is dosed for 4-7 half-lives of a drug. For Antibody 51, the terminal elimination half-life in rats is ~6 days (unpublished finding). In humans the ch-Antibody 51 terminal elimination half-life could be 2-4 weeks.

The results of this study suggest administration of high affinity murine anti-METH-antibody Antibody 51 can change the responding to a (±)-METH induced relapse in rats. The effects were dependent on the dose of Antibody 51 administered and the number of previous Antibody 51 administrations. The effects on responding continued even after Antibody 51 administration was ceased (on Days 10 and 13), suggesting a prolonged efficacy beyond the actual administration. While the two lower doses of mAb initially increased the number of lever presses, before converging to the apparent control levels of responding, the highest dose of Antibody 51 (100 mg/kg) reduced responding below control levels after the second administration. Since the relapse to METH responding was induced by the use of the stereoisomer (±)-METH, these data suggest anti-(+)-METH antibody Antibody 51 can still be effective against (+)-METH-induced behavior even when the (−)-METH is present. Finally, these data show the effectiveness against (±)-METH-induced relapse was improved with increasing numbers of mAb7F9 administrations.

Example 4

Prevention of METH-Induced Relapse in Rats

Chimeric Antibody 51 (ch-Antibody 51) is based on the murine parent antibody, Antibody 51, and is a chimeric antibody, as the term is used in the art. ch-Antibody 51 is a chimeric monoclonal antibody designed bind to (+)-methamphetamine (METH) and some structurally related stimulants (i.e., (+)-amphetamine and (+)-MDMA) efficiently within the human body. Ch-Antibody 51 was designed to maintain the variable framework regions of the heavy and light chains of the mouse antibody including all three CDRs of both the heavy and the light chains, but includes a human IgG2 Fc region. These studies were designed to examine the potential for ch-Antibody 51 to bind to structurally-related stimulants, neurotransmitters, selected medications, and other drugs of abuse (Table 4). The assay used a modified radioimmunoassay (RIA) in a competitive binding format with [$^3$H]-METH (similar to RIA in Peterson et al., J $Pharmacol$ $Exp$ $Ther$ (2008) 325:124-133) The assay is started by incubating radiolabeled METH ([$^3$H]-METH) with unlabeled potential ligand (concentrations typically range from 0.03-5000 nM), ch-Antibody 51, and Protein G conjugated to magnetic beads. After reaching equilibrium, the beads with bound antibody and ligand are separated from the solution with a magnet and the supernatant aspirated. The amount of mAb-bound [$^3$H]-METH is quantified by liquid scintillation counting. For each of the related stimulants, a complete inhibition curve was constructed to determine the $K_D$ or $K_I$ value (see FIG. 7). For the remaining test ligands, the same method was used, but only 2 concentrations of ligand were tested rather than the expanded range. Additionally, highly concentrated pools of compounds were used to attempt inhibition of [$^3$H]-METH binding to ch-Antibody 51. If METH binding was inhibited 50% or more by any pool of ligands, the assay was repeated with the compounds separately to identify the individual cross reacting ligands.

Average disintegrations per minute (DPM) from the scintillation counter were plotted versus the concentration of unlabeled ligand using Origin software (OriginLab). A 4-parameter logistic function was fit to the data to obtain values describing the top and bottom plateaus, slope and mid-point. The mid-point of the curve identifies the concentration of unlabeled ligand required to inhibit 50% of the binding of [$^3$H]-METH. For homologous assays in which unlabeled METH competes with [$^3$H]-METH for binding to ch-Antibody 51, the dissociation constant ($K_D$) is found by subtracting the concentration of [$^3$H]-METH from the mid-point. For non-homologous assays in which unlabeled ligands other than METH compete for binding with [$^3$H]-METH, the subtraction yields a $K_I$ value.

Each of the structurally related stimulants listed in Table 4 was tested individually, over a range of concentrations, as an inhibitor of radiolabeled METH binding. The resulting data was used to determine ch-Antibody 51's dissociation constant ($K_D$, which is the inverse of the affinity constant) or $K_I$ (concentration of ligand [e.g., inhibitor] which prevents 50% of the [$^3$H]-METH from binding) for the specific ligand. The FIG. 7 illustrates a typical curve that results from such experiments.

These results were compared to those from the murine parent antibody, Antibody 51, to show retention of the binding profile after conversion to a chimeric mouse-human form. Based on the ligand binding characteristics, there was good agreement between the murine and chimeric forms of the antibody suggesting that the efficacy data from the murine form is relevant and predictive of the chimeric. Each experiment was conducted in triplicate and has been repeated two (AMP and MDMA) or three (METH) times to give the average $K_D$ or $K_I$ value shown in Table 5.

TABLE 5

Results from related stimulant cross-reactivity testing.

| Ligand | ch-Antibody 51 | Antibody 51 |
|---|---|---|
| (+)-Methamphetamine | $K_D$ = 6.88 nM | $K_D$ = 6.88 nM |
| (+)-Amphetamine | $K_I$ = 164 nM | $K_I$ = 181 nM |
| (+)-MDMA | $K_I$ = 6.69 nM | $K_I$ = 7.93 nM |

Results from the pools of potential ligands are presented in Table 6. Each pool was analyzed in triplicate, twice at each concentration.

TABLE 4

Ligands tested for ch-Antibody 51 cross-reactivity

| Related stimulants | Neurotransmitters* | Medications* | Drugs of abuse* |
|---|---|---|---|
| (+)-Methamphetamine | Dopamine | (+)-Pseudoephedrine | (−)-MDMA |
| (+)-Amphetamine | (-)-Norepinephrine | (+)-Norpseudoephedhrine | (+)-MDA |
| (+)-MDMA | (-)-Epinephrine | (−)-Phenylephrine | Cocaine |
| | Serotonin | (±)-Ephedrine | Morphine |
| | γ-aminobutyric acid | 2-Phenylethylamine | PCP |
| | L-Glutamate | Tyramine | |

*Multiple potential ligands were pooled in groups outlined by black boxes. Each ligand was present at 1 μM and 10 μM (final concentration).

TABLE 6

Results from ligand cross-reactivity testing

| Ligand pool | Concentration of each inhibitor in pool | Percent inhibition of [$^3$H]-METH binding |
|---|---|---|
| Dopamine | 1 μM | 2.1 |
| (−)-Norepinephrine | 10 μM | 4.3 |
| (−)-Epinephrine | | |
| Serotonin | 1 μM | 1.0 |
| γ-aminobutyric acid | 10 μM | 1.6 |
| L-Glutamate | | |
| (+)-Pseudoephedrine | 1 μM | 53.5 |
| (+)-Norpseudoephedrine | 10 μM | 92.3 |
| (−)-Phenylephrine | | |
| (±)-Ephedrine | 1 μM | 37.0 |
| 2-Phenylethylamine | 10 μM | 86.3 |
| Tyramine | 1 μM | 2.1 |
|  | 10 μM | 7.5 |
| (−)-MDMA | 1 μM | 75.7 |
| (+)-MDA | 10 μM | 98.9 |
| Cocaine | 1 μM | 3.2 |
| Morphine | 10 μM | 1.5 |
| PCP | | |

Three (3) of the pools inhibited binding of radiolabeled METH by more than 50%, therefore these individual ligands were retested at 1 μM in triplicate in 2 separate assays. The average results are reported in Table 7.

TABLE 7

Results from individual ligand cross-reactivity testing at 1 μM

| Individual ligands | Percent inhibition of [$^3$H]-METH binding |
|---|---|
| (+)-Pseudoephedrine | 5.1 |
| (+)-Norpseudoephedrine | 36.3 |

TABLE 7-continued

Results from individual ligand cross-reactivity testing at 1 μM

| Individual ligands | Percent inhibition of [$^3$H]-METH binding |
|---|---|
| (−)-Phenylephrine | 38.2 |
| (±)-Ephethine | 26.1 |
| 2-Phenylethylamine | 20.0 |
| (−)-MDMA | 78.3 |
| (+)-MDA | 40.7 |

Since only (−)-MDMA was capable of inhibiting [$^3$H]-METH binding at more than 50% when tested individually, it is the only ligand with a $K_I$ of less than 1 μM. All other ligands tested must be present at concentrations greater than 1 μM to have an appreciable effect on the binding capacity of ch-Antibody 51. Ecstasy is a racemic mixture of the (+) and (−) isoforms of (±)-MDMA. They are structural analogs of (±)-METH, therefore some cross reactivity is expected. The ability of ch-Antibody 51 to bind both forms of MDMA may actually improve its utility as a treatment for MDMA abuse in the future.

The ligand cross reactivity profile for ch-Antibody 51 was examined using a modified radioimmunoassay and selected potential ligands. As expected, ch-Antibody 51 and Antibody 51 have very similar binding profiles for the structurally related stimulants, especially for (+)-METH. This suggests that the efficacy data obtained from studies of Antibody 51 in rodents should be useful and predictive in evaluating the potential for using ch-Antibody 51 to treat METH abusing subjects. In summary, the ch-Antibody 51 binding profile is limited to METH and structurally similar stimulants. The lack of cross reactivity with tested medications, neurotransmitters, and other drugs of abuse suggests that ch-Antibody 51 is not likely to interact with common substances in the body of a size similar to METH.

What is claimed is:

1. An isolated antibody, wherein the antibody specifically binds (+) methamphetamine and comprises:
   (a) a light chain CDR1 comprising the amino acid sequence of SEQ ID NO: 5;
   (b) a light chain CDR2 comprising the amino acid sequence of SEQ ID NO:6;
   (c) a light chain CDR3 comprising the amino acid sequence of SEQ ID NO: 7;
   (d) a heavy chain CDR1 comprising the amino acid sequence of SEQ ID NO: 8;
   (e) a heavy chain CDR2 comprising the amino acid sequence of SEQ ID NO: 9; and
   (f) a heavy chain CDR3 comprising the amino acid sequence of SEQ ID NO:10.

2. The isolated antibody of claim 1, wherein the antibody is encoded by a nucleic acid sequence comprising a sequence selected from the group consisting of SEQ ID NO:1 and SEQ ID NO:2.

3. The isolated antibody of claim 1, wherein the antibody is selected from the group consisting of a single-chain antibody, an immunologically effective antibody fragment thereof, a chimeric antibody, and a humanized antibody.

4. A method for treating at least one medical problem associated with methamphetamine use in a subject which comprises administering an effective amount of the antibody of claim 1 to the subject to treat at least one medical problem.

5. The method of claim 4, wherein the treating includes attenuating, reversing, or improving at least one symptom or sign of methamphetamine use in a subject.

6. The method of claim 4, wherein the medical problem associated with methamphetamine use is selected from the group consisting of methamphetamine addiction and methamphetamine abuse.

7. The method of claim 4, wherein the medical problem associated with methamphetamine use is selected from the group consisting of acute methamphetamine overdose, chronic methamphetamine overdose, and methamphetamine-use relapse.

8. The method of claim 4, wherein the anti-(+) methamphetamine antibody binds an epitope within (+) methamphetamine, a metabolite of (+) methamphetamine, or (+) methamphetamine-like analog.

9. The method of claim 4, wherein the antibody slows the rate of (+) methamphetamine entry into the brain of a subject.

10. The method of claim 4, wherein the antibody reduces the frequency of methamphetamine use relapse in a subject addicted to methamphetamine.

11. An isolated bispecific antibody, wherein the antibody specifically binds at least (+) methamphetamine and comprises:
   (a) a light chain CDR1 comprising the amino acid sequence of SEQ ID NO: 5;
   (b) a light chain CDR2 comprising the amino acid sequence of SEQ ID NO:6;

(c) a light chain CDR3 comprising the amino acid sequence of SEQ ID NO: 7;
(d) a heavy chain CDR1 comprising the amino acid sequence of SEQ ID NO: 8;
(e) a heavy chain CDR2 comprising the amino acid sequence of SEQ ID NO: 9; and
(f) a heavy chain CDR3 comprising the amino acid sequence of SEQ ID NO:10.

* * * * *